US008546095B2

(12) United States Patent
Tumlin et al.

(10) Patent No.: US 8,546,095 B2
(45) Date of Patent: Oct. 1, 2013

(54) METHODS FOR DETERMINATION OF CALCINEURIN ACTIVITY AND USES IN PREDICTING THERAPEUTIC OUTCOMES

(75) Inventors: James Tumlin, Signal Mountain, TN (US); Allan D. Kirk, Atlanta, GA (US); Brian R. Roberts, Sandy Springs, GA (US); Jennifer Gooch, Lilburn, GA (US)

(73) Assignee: Emory University, Atlanta, GA (US)

( * ) Notice: Subject to any disclaimer, the term of this patent is extended or adjusted under 35 U.S.C. 154(b) by 638 days.

(21) Appl. No.: 12/690,146

(22) Filed: Jan. 20, 2010

(65) Prior Publication Data

US 2010/0159475 A1  Jun. 24, 2010

Related U.S. Application Data

(63) Continuation of application No. 12/669,665, filed as application No. PCT/US2008/071726 on Jul. 31, 2008, now abandoned.

(60) Provisional application No. 60/962,884, filed on Aug. 1, 2007.

(51) Int. Cl.
*G01N 33/00* (2006.01)
*G01N 33/53* (2006.01)
*G01N 1/18* (2006.01)
*A61K 49/00* (2006.01)

(52) U.S. Cl.
USPC .............. 435/7.72; 435/6; 435/7.24; 435/7.4; 435/21; 436/518; 436/523; 436/545; 436/546; 436/171; 436/172; 436/177; 436/811; 424/9.2

(58) Field of Classification Search
USPC ................ 435/6, 7.1, 7.2, 7.24, 7.4, 7.72, 21; 436/504, 518, 523, 545, 546, 171, 172, 811, 436/177; 424/9.2
See application file for complete search history.

(56) References Cited

U.S. PATENT DOCUMENTS 6,057,333 A   5/2000   Gunaskera et al.
6,444,870 B1  9/2002   Zhang et al.
(Continued)

FOREIGN PATENT DOCUMENTS

EP   1100912 B1   7/2004
WO   9612806      5/1996
(Continued)

OTHER PUBLICATIONS

Boleslawski et al. Defective Inhibition of Peripheral CD8+ T Cell IL-2 Production by Anti-Calcineurin Drugs Druing Acute Liver Allograft Rejection, Transplantation 77 (12): 1815-1820 (Jun. 27, 2004).*

(Continued)

*Primary Examiner* — Gail R Gabel
(74) *Attorney, Agent, or Firm* — Emory Patent Group; James C. Mason; Susanne Hollinger

(57) ABSTRACT

The methods of the disclosure provide fluorescence-based assays for calcineurin activity, especially in isolated T cells. The methods include the stimulation of the T cells with agents that specifically target the TCR with or without influencing co-stimulatory pathways. One TCR agonist is monoclonal antibodies specific for CD3, which more precisely distinguish the inducible activity of calcineurin than does an alternative method targeting the T cell receptor (CD3) combined with CD28 costimulation. This method more accurately distinguishes between the measured level of calcineurin activity of T cells from immunosuppressed transplant recipients and normal individuals, and thus has improved diagnostic accuracy with respect to the response of an individual to immunosuppressant therapy following an organ transplant.

11 Claims, 24 Drawing Sheets

(56) References Cited

U.S. PATENT DOCUMENTS

| | | | |
|---|---|---|---|
| 6,569,867 B2 | 5/2003 | Chu et al. |
| 6,605,593 B1 | 8/2003 | Naicker et al. |
| 6,613,739 B1 | 9/2003 | Naicker et al. |
| 6,624,302 B2 | 9/2003 | Reeves et al. |
| 6,784,156 B2 | 8/2004 | Or et al. |
| 6,809,077 B2 | 10/2004 | Or et al. |
| 6,875,581 B1 | 4/2005 | Voelkel |
| 6,977,141 B2 | 12/2005 | Yuan et al. |
| 6,979,671 B2 | 12/2005 | Or et al. |
| 7,012,064 B2 | 3/2006 | Or et al. |
| 7,012,065 B2 | 3/2006 | Or et al. |
| 7,202,050 B2 | 4/2007 | Auld |
| 2003/0045679 A1 | 3/2003 | Crawford |
| 2005/0074438 A1 | 4/2005 | Kim et al. |
| 2007/0190588 A1 | 8/2007 | Ornatsky |
| 2010/0159475 A1 | 6/2010 | Tumlin et al. |

FOREIGN PATENT DOCUMENTS

| | | | |
|---|---|---|---|
| WO | WO 2007/022074 | * | 2/2007 |
| WO | WO2007022074 A2 | | 2/2007 |
| WO | 2009141121 | | 11/2009 |

OTHER PUBLICATIONS

Batiuk et al. Evidence that Calcineurin is Rate-Limiting for Primary Human Lymphocyte Activation, J. Clin. Invest. 100(7): 1894-1901 (Oct. 1997).*

Manninen et al. Synergistic activation of NFAT by HIV-1 Nef and the Ra/MAPK Pathway, The Journal of Biological Chemistry 275 (22): 16513-16517 (Jun. 2000).*

Supplemental European Search Report dated Oct. 28, 2010.

Enz, et al., "Nonradioactive Assay for Protein Phosphatase 2B (Calcineurin) Activity Using a Partial Sequence of the Subunit of cAMP-Dependent Protein Kinase as Substrate," Analytical Biochemistry 216, pp. 147-153 (1994).

Roberts, et al., "A Fluorimetric Method for Determination of Calcineurin Activity," Cell Calcium 43 (2008) pp. 515-519.

Biomol Green Calcineurin Assay Kit: Catalog No. AK-804, 2004.

Calbiochem Calcineurin Assay Kit: Catalog No. 207005, Dec. 2007.

Calbiochem Calcineurin Assay Kit: Catalog No. 207007, Jul. 2004.

Enzo Biomol Calcineurin Assay Kit: Catalog No. AK-816.

Fruman et al., 1996, Measurement of calcineurin phosphatase activity in cell extracts, Method Enzymol. 9: pp. 146-154.

GenBank Accession No. AAN88706, Sep. 2002.

GenBank Accession No. AAY08279, Apr. 2005.

GenBank Accession No. ABE13331, Dec. 2005.

Gooch et al., 2001, Insulin-like growth Factor induces renal cell hypertrophy via a calcineurin-dependent mechanism, J. Biol Chern. 276 : pp. 42492-42500.

Gooch et al., 2004, Involvement of calcineurin in transforming growth factor-beta-mediated regulation of extracellular matrix accumulation, J. Biol Chern. 279: pp. 15561-15570.

Gooch et al., Calcineurin A-alpha but not A-beta is required for normal kidney development and function, Am. J. Pathol. 165: pp. 1755-1765, (2004).

Gooch et al., 2004, Calcineurin is activated in diabetes and is required for glomerular hypertrophy and ECM accumulation, Am. J. Physiol. Renal. Physiol. 284: F144-FI54.

Koefoed-Nielsen, P.B., et al., 2004, Validation of the Calcineurin Phosphatase Assay. Clinical Chemistry, 50: pp. 2331-2337.

Kupcho et al., 2004 A Homogeneous, Nonradioactive, High-Throughput Fluorogenic Protein Phosphatase Assay. Journal of Biomolecular Screening, 9: pp. 223-231.

Kuroda et al., 2004 Phosphopeptide-selective column-switching RP-HPLC with a titania precolumn, Anal Sci. 20: pp. 1313-1319.

Pinkse et al., 2004, Selective isolation at the femtomole level of phosphopeptides from proteolytic digests using 20-NanoLC-ESI-MS/MS and titanium oxide precolumns, Anal. Chern. 76: pp. 3935-3943.

Promega 2009, ProFluor Ser/Thr PPas Assay Technical Bulletin Part #TB324.

Sellar et al., 2006, Spectrophotometric assay for calcineurin activity in leukocytes isolated from human blood. Analytical Biochemistry, 358: pp. 104-110.

* cited by examiner

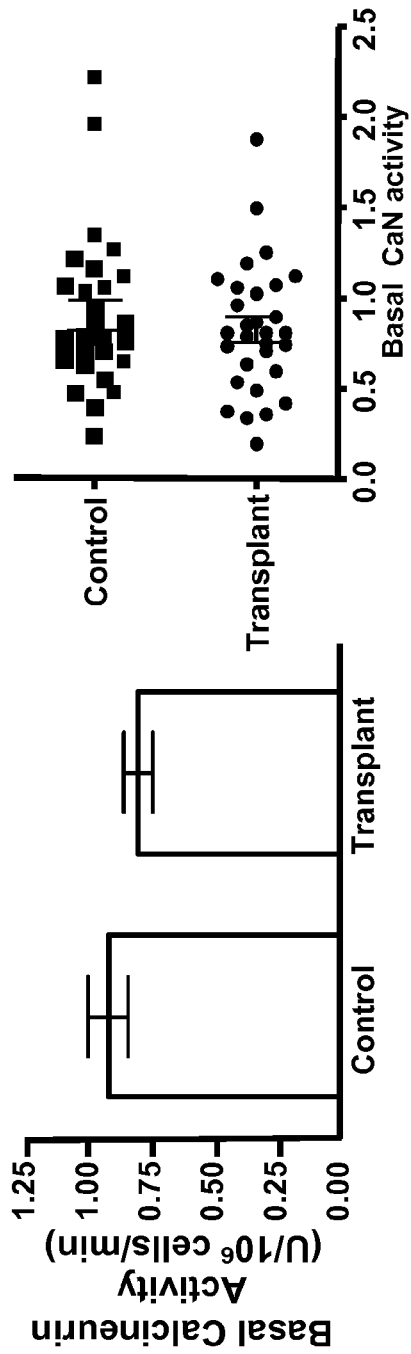
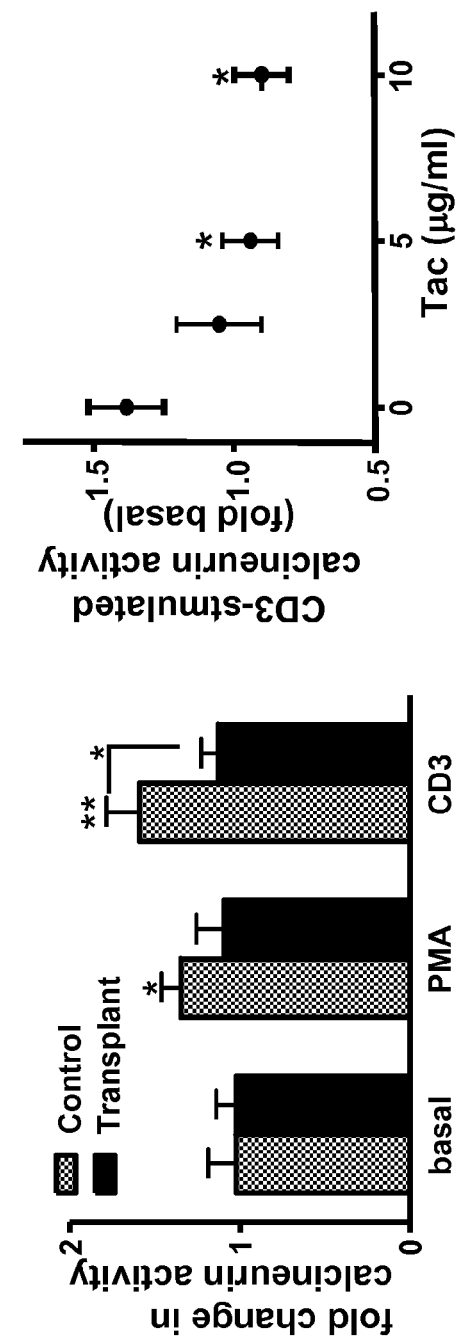
Fig. 10A, Fig. 10B, Fig. 10C, Fig. 10D

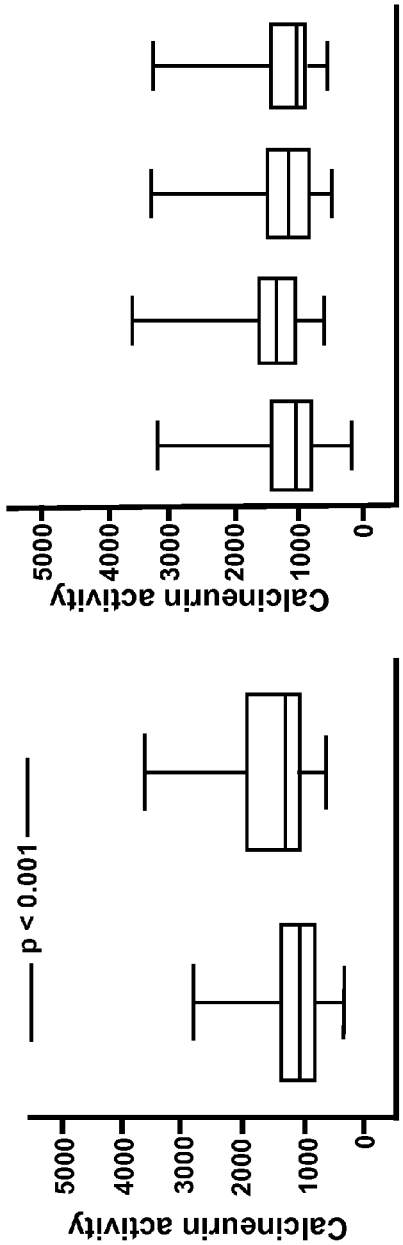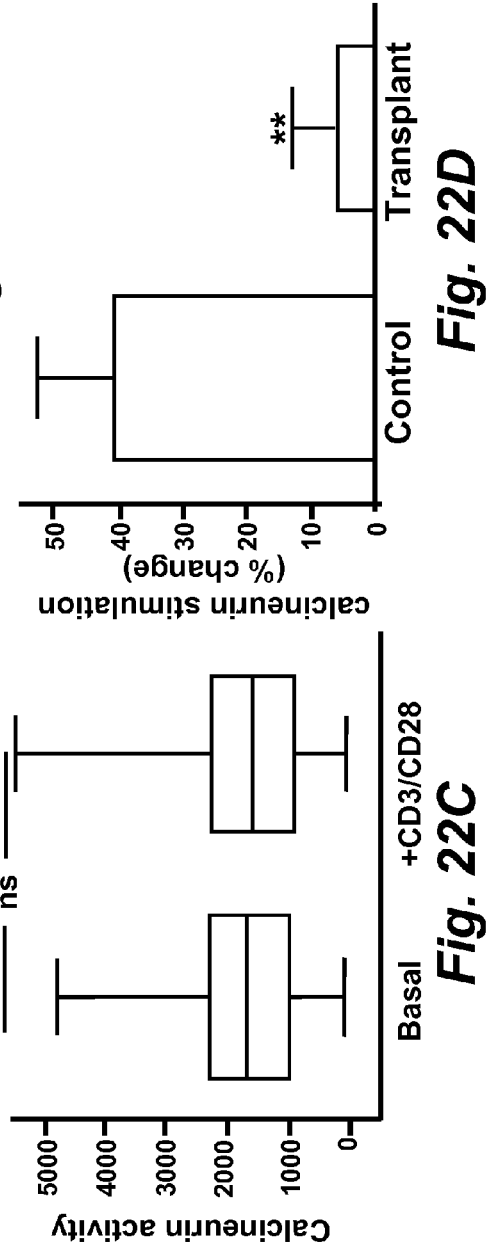
Fig. 22A  Fig. 22B  Fig. 22C  Fig. 22D

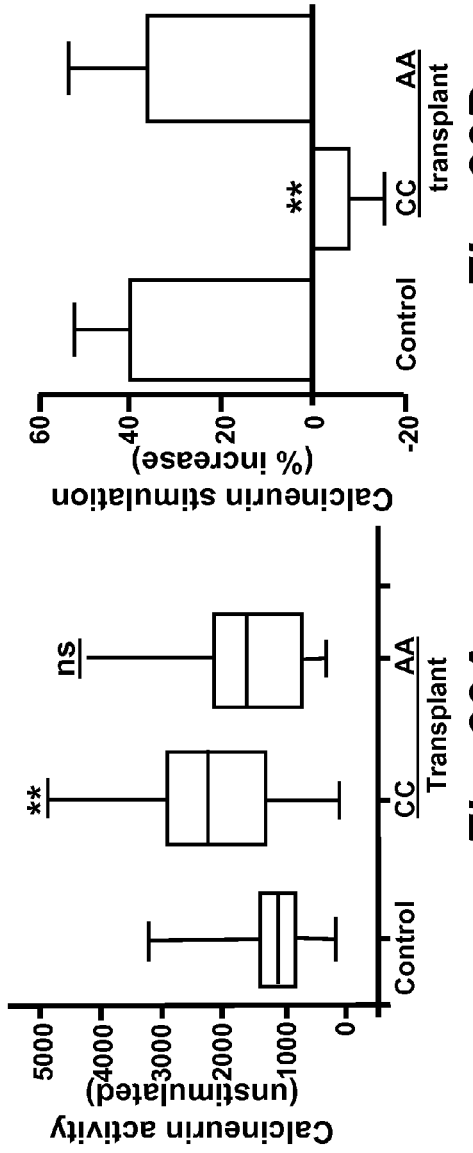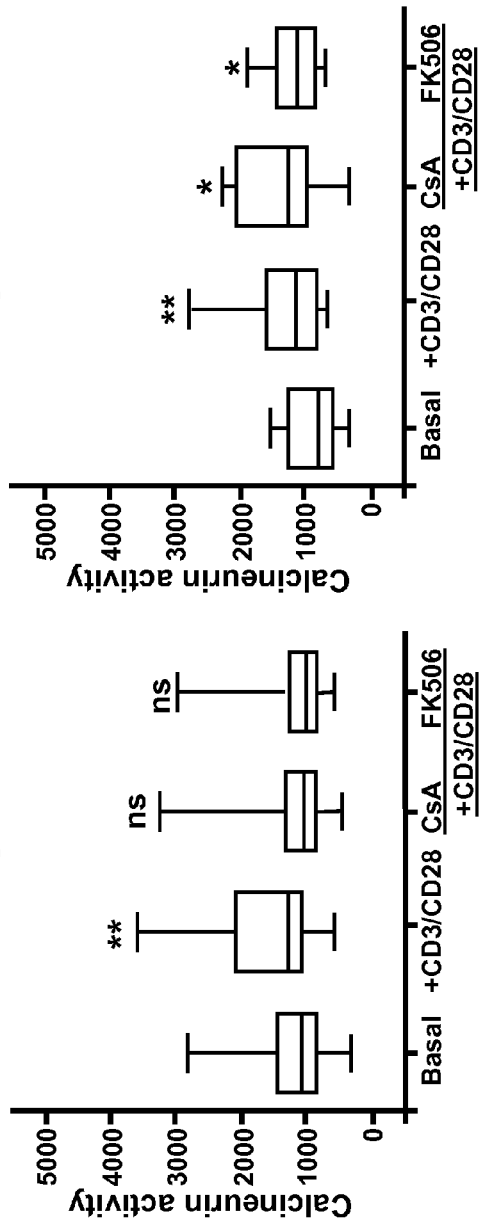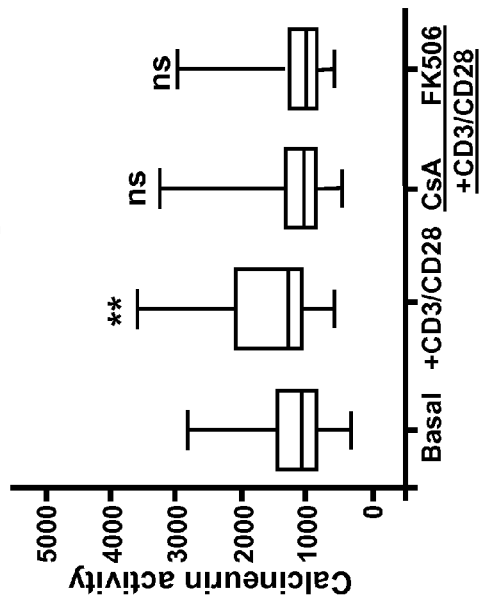
Fig. 23A Fig. 23B Fig. 23C Fig. 23D

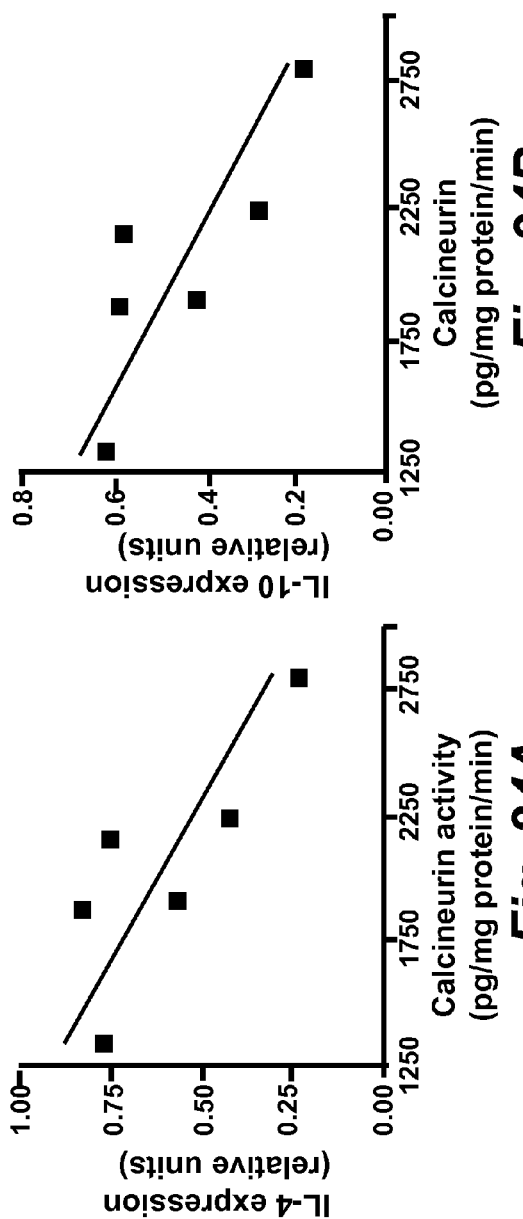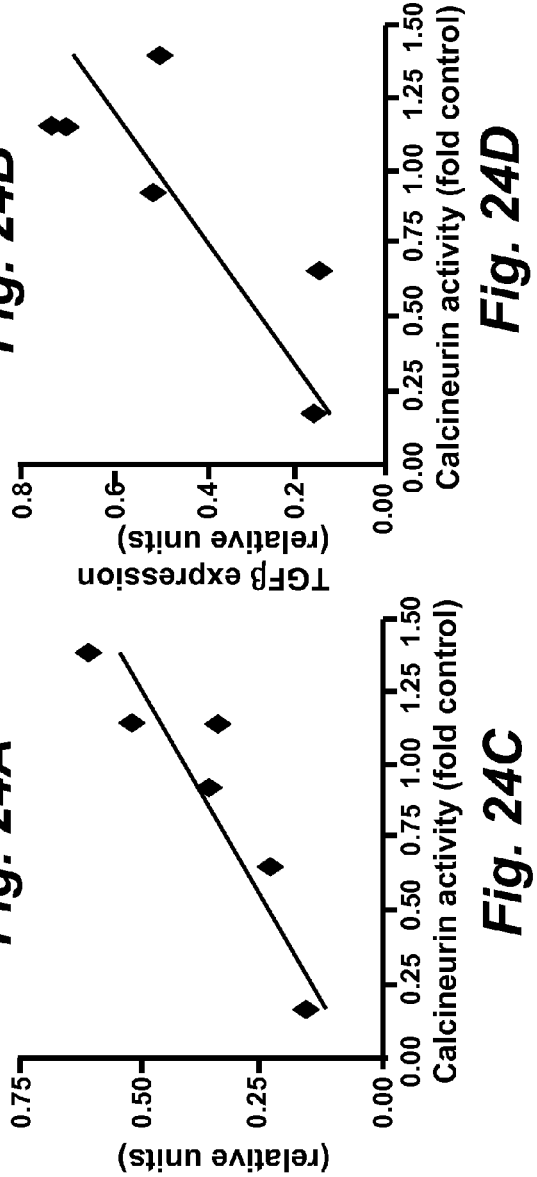

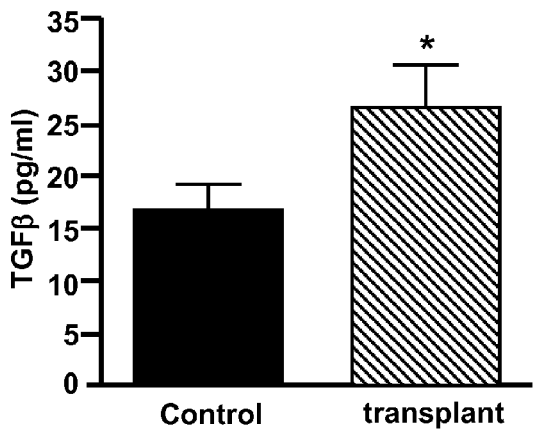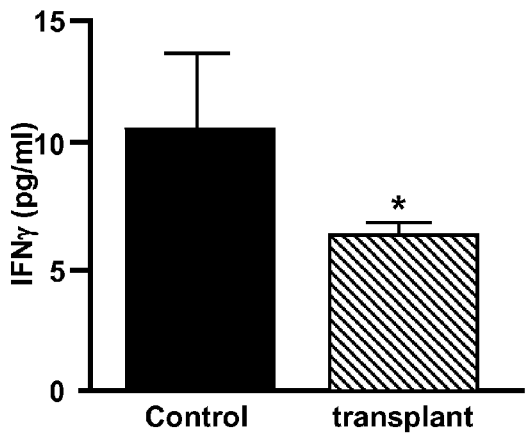
*Fig. 25A* *Fig. 25B*
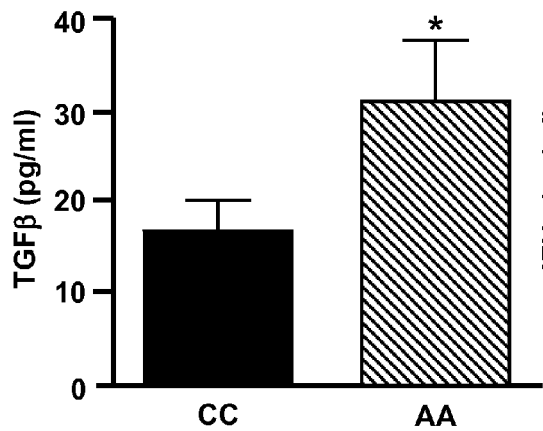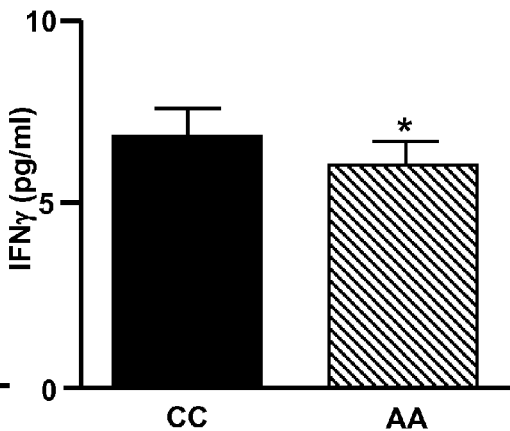
*Fig. 25C* *Fig. 25D*

METHODS FOR DETERMINATION OF CALCINEURIN ACTIVITY AND USES IN PREDICTING THERAPEUTIC OUTCOMES

CROSS-REFERENCE TO RELATED APPLICATIONS

This application is a continuation-in-part of co-pending U.S. patent application Ser. No. 12/669,665 entitled "METHODS FOR DETERMINATION OF PROTEIN PHOSPHATASE ACTIVITY AND USES IN PREDICTING THERAPEUTIC OUTCOMES" filed Jan. 19, 2010, which itself claims priority to U.S. Provisional Patent Application Ser. No. 60/962,884 entitled "ASSAY TO MEASURE PHOSPHATASE ACTIVITY" and filed Aug. 1, 2007, and to PCT Application Serial No.: PCT/US2008/071726 entitled METHODS FOR DETERMINATION OF PROTEIN PHOSPHATASE ACTIVITY AND USES IN PREDICTING THERAPEUTIC OUTCOMES" and filed Jul. 31, 2008, the entireties of which are hereby incorporated by reference.

STATEMENT ON FUNDING PROVIDED BY THE U.S. GOVERNMENT

This invention was made with government support under NIH Grant No. R01 DK066422 awarded by the U.S. National Institutes of Health of the United States government. The government has certain rights in the invention.

FIELD OF THE DISCLOSURE

This disclosure relates to methods of clinical monitoring of calcineurin activity and immunosuppression in patients, and for predicting transplant acceptance in patients.

BACKGROUND

Calcineurin is a calcium-dependent, serine/threonine phosphatase that is a signal transduction mediator involved in a variety of pathways identified in T cells. There are three isoforms of the catalytic subunit of calcineurin-$\alpha$, $\beta$, and $\gamma$. Unique and distinct roles for the $\alpha$ and $\beta$ isoforms have been identified. Importantly, the $\beta$ isoform appears to be the primary isoform required for normal activity of T cells.

The addition of the calcineurin inhibitors cyclosporine A and FK506 to immunosuppressive regimens reduces the incidence of acute allograft rejection and effectively doubles one-year survival of kidney transplant patients. However, long-term graft survival has improved far less significantly, with only 66% and 78% of deceased-donor kidney and living-donor kidney recipients, respectively, surviving 5 years. This statistic is even more striking when considered for different racial groups. Eighty percent of Caucasians who receive living-donor organs survive for 5 years while only 64% of African Americans live that long. Similar trends are observed for recipients of deceased-donor organs; there is a 70% survival rate for Caucasians but only 55% for African Americans. Understanding mechanisms that contribute to disparate outcomes for transplant patients is an area of tremendous importance. Despite considerable effort, no consensus on the underlying causes has been reached that adequately explains racial disparities in long-term outcomes.

Cyclosporine A (cyclosporine A) and FK-506 (tacrolimus) are structurally unrelated compounds that form drug-receptor complexes with immunophilins (cyclophilin-18 and FKBP-12 respectively) and potently inhibit calcineurin phosphatase activity. The wide spread use of cyclosporine A and tacrolimus in the past two decades has markedly reduced the frequency of acute allograft rejection and prolonged patients survival. Despite their proven benefits, monitoring of cyclosporine A and tacrolimus levels in a patient has proven to be a poor clinical indicator of transplant outcomes. Some patients experience rejection in the presence of adequate or even excessive blood concentrations (Caruso et al., (2001) Clin. Chem. 47: 1679-1687), whereas others develop toxicity even when blood trough concentrations are low (Citterio F. (2004) Transplant. Proc. 36: 420S-425S; Kahan B. D. (2004) Transplant. Proc. 36: 378S-391S). However, in the absence of an alternative means of monitoring calcineurin inhibitor efficacy, current treatment protocols continue to rely upon plasma drug levels for therapeutic monitoring and optimizing immunosuppression.

One potential alternative to plasma drug level monitoring is direct assay of calcineurin activity. However, few studies have directly examined calcineurin activity in T cells or investigated the effects of calcineurin inhibitors on enzyme activity. Studies of calcineurin activity in vivo have focused on issues including pharmacodynamics in response to cyclosporine and tacrolimus (Koefoed-Nielsen & Jorgensen (2002) Transplant. Proc. 34: 1743-1744; Koefoed-Nielsen et al., (2006) Transpl. Int. 19: 821-827; Koefoed-Nielsen et al., (2005) Transplant. Proc. 37: 1736-1738; Mortensen et al., (2006) Transplant. Proc. 38: 2651-2653.) and possible effects of variables including gender and time of day (Koefoed-Nielsen et al., (2005a) Scand. J. Immunol. 62: 309-311).

In an early study using transplant patients, Batiuk et al., ((1997) J. Clin. Invest. 100: 1894-1901) used a $^{32}PO_4$-labeled calcineurin specific substrate to measure the effects of cyclosporine A on calcineurin activity in 30 renal allograft recipients. In vivo measurements demonstrated that calcineurin activity was inhibited by up to 80% one hour after an oral dose of cyclosporine A, but only 20-30% within four hours. However, the degree of enzyme inhibition and the effect on cytokine production varied greatly between individuals. In a similar study, Pai et al., ((1994) Blood 84: 3974-3979) examined the long-term effect of cyclosporine A on calcineurin activity in peripheral lymphocytes from bone marrow transplant patients. While cyclosporine A initially inhibited calcineurin activity during the first 100 days of transplantation, enzyme activity progressively rose over time and within 6 months was similar to non-transplant controls.

Calcineurin is unique among phosphatases in that its activity is calcium-dependent and is central to T cell receptor (TCR) signaling and amplification of immune responses. The activation of the TCR complex leads to the release of intracellular calcium and calcineurin-mediated dephosphorylation of transcription factors that regulate IL-2 and other pro-inflammatory cytokines (Macian F. (2005) Nat. Rev. Immunol. 5: 472-484). Calcineurin is known to be activated downstream of the T cell receptor and regulates transcription factors including the Nuclear Factor of Activated T cells (NFATc). NFATc proteins, in turn, control expression of cytokines including IL-2 and IL-4. Blockade of calcineurin/ NFAT activity inhibits T cell activity and results in immune suppression. Although cyclosporine A has been clinically used for more than 20 years and FK506 over a decade, appropriate and effective target blood levels for maintenance immunosuppression have yet to be properly defined. Discrepancies between calcineurin inhibitor dose and clinical immune suppression suggest that calcineurin activity itself may be a source of variability. However, there have been only limited studies that directly measure calcineurin activity, and there is no data regarding factors which may affect the calcineurin sensitivity to inhibition by cyclosporine A and FK506.

SUMMARY

Stimulation of the T cell receptor (TCR) with anti-CD3/anti-CD28 antibodies results in an increase in calcineurin activity levels in T cells from control patients not subject to immunosuppressant therapy, but not in T cells from transplant recipient subjects in the midst of a therapeutic course calcineurin inhibitor treatment. The present disclosure provides methods to measure calcineurin activity in transplant and control subjects after T cell receptor stimulation, thereby detecting changes in calcineurin activity that can be correlated with therapeutic benefits of calcineurin inhibitors.

The methods of the disclosure include the stimulation of peripheral blood mononuclear cells (PBMCs), and in particular T cells, with agents that specifically target the TCR with or without influencing costimulatory pathways. One example is monoclonal antibodies specific for CD3 alone, which more precisely distinguish the inducible activity of calcineurin than does an alternative method targeting the T cell receptor (CD3) combined with CD28 costimulation. This method more accurately distinguishes between immunosuppressed transplant recipients and normal individuals, and thus has improved diagnostic accuracy. The ability to better detect and measure an aspect of calcineurin function that is directly altered with calcineurin inhibitor use is an advance toward therapeutic monitoring of calcineurin activity.

One aspect of the present disclosure encompasses methods for determining the response of a human or animal subject to an immunosuppressive therapeutic agent, embodiments of the methods comprising: (i) obtaining an isolated population of T cells from a human or animal subject in receipt of an immunosuppressive therapeutic agent; (iii) lysing the isolated population of T cells; (ii) dividing the lysed isolated T cell population into at least a first aliquot and a second aliquot; (iv) determining a first level of calcineurin activity in the first aliquot of lysed T cells; (v) contacting the second aliquot of lysed T cells with a composition comprising a T cell receptor agonist and then determining a second level of calcineurin activity in the second aliquot of lysed T cells; and (vi) comparing the first and the second levels of calcineurin activity as determined in steps (iv) and (v), respectively, whereby the ratio of the first and the second levels of calcineurin activity indicates the degree of responsiveness by the human or animal subject to the immunosuppressive therapeutic agent.

In embodiments of this aspect of the disclosure, the prediction of the response of a human or animal subject to an administered immunosuppressive therapeutic agent can provide a prognosis of a transplant in the human or animal subject.

In embodiments of the methods of this aspect of the disclosure, the T cell agonist can be an anti-CD3-specific antibody.

In some embodiments of this aspect of the disclosure, the composition comprising a T cell receptor agonist may further comprise a T cell co-stimulator. In these embodiments, the T cell co-stimulator can be, but is not limited to, an anti-CD28-specific antibody.

In the embodiments of this aspect of the disclosure, the first and the second levels of calcineurin activity may be determined by a radiometric assay or by a fluorimetric assay.

In some embodiments of the methods of this aspect of the disclosure, the fluorimetric assay may be a FRET-based fluorimetric assay.

In an embodiment of the disclosure, the composition comprising a T cell receptor agonist does not comprise a T cell co-stimulator, and the first and the second levels of calcineurin activity can be determined by a FRET-based fluorimetric assay.

In embodiments of the disclosure, the human or animal subject is a transplant recipient.

In some embodiments of this aspect of the disclosure, the fluorimetric assay may comprise the steps of: (a) contacting in a reaction mix the first aliquot of lysed T cells and a fluorescently labeled phosphorylated target peptide substrate capable of being dephosphorylated by calcineurin, wherein the target peptide comprises an amino acid sequence selected from SEQ ID NO.: 1 and SEQ ID NO.: 2, under conditions allowing calcineurin to dephosphorylate the target peptide; (b) contacting the reaction mix with a titanium oxide matrix, thereby partitioning phosphorylated target peptide from dephosphorylated target peptide; and (c) determining the intensity of the fluorescence of the fluorescently labeled dephosphorylated target peptide, thereby detecting calcineurin activity; and (d) correlating the intensity of the fluorescence to the calcineurin activity, said correlating step comprising: (i) providing a test sample, wherein the test sample comprises a known amount of calcineurin activity, and repeating steps (a)-(f) on said test sample, thereby obtaining a value of the second fluorescence intensity corresponding to the known amount of the calcineurin; and (ii) comparing a value of the second fluorescence intensity generated from an aliquot of lysed T cells with the value of the second fluorescence intensity obtained with the known amount of calcineurin, thereby determining the amount of calcineurin activity in the aliquot of isolated T cells.

In these embodiments, step (b) may comprise: (i) obtaining a reaction vessel, wherein the reaction vessel is coated with a titanium oxide matrix, and wherein the titanium oxide matrix is contacted with a binding buffer; (ii) delivering the reaction mix to the coated vessel, and incubating under conditions allowing binding of fluorescently labeled phosphorylated peptide to the titanium oxide matrix; (iii) transferring the reaction mix from the coated well to a vessel containing ammonium hydroxide; and (iv) determining the amount of fluorescence emitted by fluorescently labeled dephosphorylated peptide in the reaction mix.

In embodiments of this aspect of the disclosure, the assay method can be configured for high-throughput screening of a plurality of test samples. In these embodiments, the assay method can be configured for automated high-throughput screening of a plurality of test samples.

In some of the embodiments of this aspect of the disclosure, the target peptide may have the amino acid sequence according to SEQ ID NO.: 1 and can be phosphorylated on the Ser-15 position.

In one embodiment, the target peptide is capable of being specifically dephosphorylated by the β-isoform of calcineurin, and comprises the amino acid sequence according to SEQ ID NO.: 2, wherein the S-6 position is phosphorylated.

In other embodiments of this aspect of the disclosure, the fluorimetric-based assay can be a FRET-based fluorimetric assay can comprise: (a) providing an assay reaction mix comprising a target peptide comprising an amino acid sequence specifically recognized by calcineurin, wherein the target peptide comprises the amino acid sequence SEQ ID NO.: 1 or SEQ ID NO.: 2, a phosphate group conjugated to said target peptide, and a first fluorophore species conjugated to said target peptide; a buffer mix configured to allow calcineurin to dephosphorylate the target peptide; and a test sample comprising an aliquot of lysed T cells; (b) incubating the assay reaction mix under conditions suitable for calcineurin to dephosphorylate the target peptide; (c) contacting the incubated reaction mix with titanium oxide, said titanium oxide having a second fluorophore species conjugated thereon, under conditions suitable for the titanium oxide to bind to a phosphorylated target peptide but not to a dephosphorylated target peptide; (d) illuminating the titanium oxide at an excitation wavelength of the second fluorophore species, whereby the second fluorophore species emits a first fluorescence, said first fluorescence exciting the first fluorophore species by FRET, thereby inducing the emission of a second fluorescence from the first fluorophore species, said second fluorescence having a wavelength different from the wavelength of the first fluorescence; (e) selectively detecting the second fluorescence, thereby detecting binding of phosphorylated target peptide to titanium oxide; (f) determining the intensity of the second fluorescence; and (g) correlating the intensity of the second fluorescence to an amount of calcineurin activity, said correlating step comprising: (i) providing a test sample comprising a known amount of calcineurin activity, and repeating steps (a)-(f) on said test sample, thereby obtaining a value of the second fluorescence intensity corresponding to the known amount of the calcineurin; (ii) comparing a value of a second fluorescence intensity generated from an aliquot of lysed T cells with the value of the second fluorescence intensity obtained with the known amount of calcineurin, thereby determining the amount of calcineurin activity in the aliquot of isolated T cells.

In embodiments of the FRET-based assay system, the titanium oxide can be formulated as micro-beads, and the micro-beads can be suspended in the assay reaction mix. In these embodiments, the assay method may be configured for automated high-throughput screening of a plurality of test samples.

In some embodiments, the target peptide can have the amino acid sequence according to SEQ ID NO.: 1, and is phosphorylated on the Ser-15 position.

In other embodiments, the target peptide can be specifically recognized and dephosphorylated by the β-isoform of calcineurin, the target peptide comprising the amino acid sequence according to SEQ ID NO.: 2, where the S-6 position is phosphorylated.

Another aspect of the disclosure encompasses kits for determining the level of calcineurin activity in a test sample, comprising a container enclosing a fluorescently labeled target peptide selectively recognizable by a calcineurin; a T cell receptor stimulator, and instructions for the use of the target peptide in determining the calcineurin activity of a test sample comprising an aliquot of lysed isolated T cells, whereby a level of calcineurin activity or a ratio of said levels indicates the degree of responsiveness by the human or animal subject to the immunosuppressive therapeutic agent.

In these embodiments of this aspect of the disclosure, the prediction of the response of a human or animal subject to an administered immunosuppressive therapeutic agent can further provide a prognosis of a transplant in the human or animal subject.

In other embodiments of this aspect of the disclosure, the kits may further comprise a titanium dioxide matrix or an amount of titanium oxide micro-beads, where the micro beads have a fluorophore conjugated thereto.

In embodiments of this aspect of the disclosure, the target peptide has an amino acid sequence selected from the group consisting of SEQ ID NOs.: 1 and 2.

In other embodiments of the kits of this aspect of the disclosure, the kits may further comprise at least one of the group consisting of a reaction buffer, a cell lysis buffer, a binding buffer, a reaction mix for phosphorylating the target peptide; an ammonium hydroxide solution; and at least one calcineurin activity standard solution.

BRIEF DESCRIPTION OF THE FIGURES

Many aspects of the disclosure can be better understood with reference to the following figures. See the text and examples for a more detailed description of the figures.

FIGS. 5A and 5B are graphs illustrating calcineurin activity in cells before and after anti-CD3/anti-CD28 antibody-stimulation, respectively. FIG. 5A: T cells were isolated from control (non-immunosuppressed patients) (n=30). FIG. 5B: T cells were isolated from post-transplant patients (n=39). T cell receptor stimulation of the control cells (FIG. 5A) resulted in a significant increase in calcineurin activity ($p<0.001$) but not with cells from the post-transplant patients (paired t test).

FIG. 5C is a graph illustrating the percentage increase in calcineurin activity determined for control subjects and transplant patients. Data shown are the mean±S.E. percentages of change in stimulated calcineurin activity for the control and transplant groups. The mean percentage of stimulated calcineurin activity was significantly less in transplant subjects compared with controls (**, p<0.001; Student's t test).

FIG. 5D is a graph illustrating IL-2 release into conditioned medium of anti-CD3/anti-CD28 antibody-treated cells was compared for control and transplant cell cohorts. There was a statistically significant decrease in the amount of IL-2 released by T cells isolated from transplant patients (**, p<0.01).

FIGS. 10A-10D are a series of graphs illustrating the measurement of calcineurin activity using a fluorimetric assay. Calcineurin activity was examined in isolated PBMCs from 30 pre-transplant control subjects and 30 post-transplant patients.

FIG. 10A is a graph illustrating the mean±SEM basal calcineurin activity for each group. There was no significant difference.

FIG. 10B is a graph illustrating the distribution of basal calcineurin activity measurements for each group. The distributions were similar.

FIG. 10C is a graph illustrating the mean±SEM fold change in calcineurin activity with PMA and CD3 stimulation for control and transplant cohorts. Control subjects responded to both PMA and CD3 with a significant increase in calcineurin activity; transplant subjects did not. (*p<0.05, **p<0.01, Two-way ANOVA).

FIG. 10D is a graph illustrating that CD3-stimulated calcineurin activity was inhibited in control PBMCs in a dose-responsive manner with increasing amounts of tacrolimus. (*p<0.05, ANOVA).

FIG. 12A is a graph showing basal calcineurin activity compared with IL-2 production in isolated T cells from a subset of transplant subjects. There was no significant association.

FIG. 12B is a graph showing TCR-stimulated calcineurin was compared with IL-2 production by linear regression. There was a significant association between stimulation of calcineurin and production of IL-2.

FIG. 14A: Reactions were carried out with 0, 0.2, or 0.3 ng of recombinant calcineurin per reaction and then the relative amount of dephosphorylated to phosphorylated peptide was determined by mass spectrometry. Data shown is the ratio of the area under the curve for dephosphorylated RII and phosphorylated RII with each condition. FIG. 14B: Reactions were performed as in FIG. 14A, and then incubated with titanium oxide matrix in a 96-well plate. After binding, the samples were removed and the relative amount of dephosphorylated to phosphorylated peptide was determined by mass spectrometry. Data shown is the ratio of the area under the curve for dephosphorylated RII and phosphorylated RII with each condition.

FIG. 15A: Calcineurin assays were performed with increasing amounts of recombinant calcineurin in the presence or absence of calcium. Recombinant calcineurin resulted in increased amounts of dephosphorylated peptide in a dose-dependent manner. This activity was dependent upon calcium. Data shown are the mean+/−SEM of triplicate reactions. FIG. 15B: Reactions containing 0.2 ng of recombinant calcineurin were carried out along with standard controls to verify calcineurin activity. Heat inactivation of the enzyme, addition of an auto inhibitory peptide, or absence of calcium all significantly reduced activity (ANOVA). Data shown are the mean+/−SEM of triplicate samples compared to a standard curve.

FIG. 16A: Cultured renal fibroblasts were treated with a variety of stimuli including arginine vasopressin (AVP), dexamethasone, and phorbol myristate acetate (PMA) to induce calcineurin activity. In addition, some cells were pre-treated with calcineurin inhibitors prior to the addition of PMA. Cells were lysed according to previously established methods and then calcineurin activity was determined. Data shown is the mean+/−SEM of triplicate samples compared to a standard curve. FIG. 16B: Mice were treated with cyclosporine A for three days to inhibit calcineurin activity and then liver and muscle samples were harvested. Tissues were lysed according to previously established methods and calcineurin activity determined. Data shown are the mean+/−SEM of triplicate samples compared to a standard curve.

In FIG. 20A, the amount of TAMRA-peptide was held constant and the amount of FLUOR-beads was increased. There was a dose-responsive increase in the FRET peak at 580 nm, and the FLUOR peak appears at 520 nm with the maximum amount of beads tested.

In FIG. 20B, the amount of FLUOR-beads was held constant and increasing amounts of TAMRA-peptide RII was added. The FRET peak at 580 nm increases in a dose-responsive fashion whereas there was no change in the FLUOR peak at 520 nm.

FIGS. 22A-22D are a series of graphs illustrating the stimulation and inhibition of calcineurin activity in healthy control subjects.

FIG. 22A shows T cells isolated from healthy control subjects (n=30), divided into equal aliquots, and then treated with DMSO as a control or anti-CD3/CD28 antibody (1 ng/ml) for 15 minutes to produce maximal calcineurin activation. Samples were then lysed and calcineurin activity determined. Data shown in each column is a box and whisker plot of control and stimulated groups. Anti-CD3/CD28 treatment resulted in a significant increase in T cell calcineurin activity (paired T-test, p<0.001).

FIG. 22B shows T cell isolates from a group of control subjects (n=30) were isolated and separated into 4 equal aliquots. Divided samples were treated with DMSO as a control, anti-CD3/CD28, or pre-treated with the calcineurin inhibitors cyclosporine A (5 µg/ml) or FK506 (tacrolimus) (5 ng/ml) prior to stimulation with anti-CD3/anti-CD28 antibodies. Lysates were obtained and calcineurin activity was determined. Data shown are box and whisker plots for each treatment group. ANOVA with Tukey's post-test indicated that anti-CD3/CD28 again produced a significant increase in calcineurin activity **p<0.001. Pre-treatments with either of the calcineurin inhibitors blocked stimulation.

FIG. 22C is a graph showing T cells isolated from post-transplant patients receiving calcineurin inhibitors (n-39), divided into equal samples and then treated with DMSO as a control or anti-CD3/anti-CD28 antibodies for 15 minutes. Samples were lysed and calcineurin activity was determined. Data are shown in a box and whisker plot for each treatment group. There was no difference in calcineurin activity with anti-CD3/anti-CD28 antibody-stimulation (paired T-test).

FIG. 22D shows the percent increase in calcineurin activity was determined for control subjects and transplant patients. Data shown are the mean±SEM of % change in anti-CD3/anti-CD28 antibody-stimulated calcineurin activity for each study participant (controls n=82, transplant patients n=39). Stimulated calcineurin activity was significantly less in transplant subjects compared to controls (T-test, **p<0.01).

FIGS. 23A-23D are a series of graphs illustrating that race is associated with differences in inhibition of anti-CD3/anti-CD28 antibody-stimulated calcineurin activity.

FIG. 23A shows basal calcineurin activity compared in control (non-transplant) subjects and transplant patients who self-identified as either Caucasian (caucasian) (n=18) or African-American (African-American) (n=19). Data are plotted in the box and whisker format. There was a significant increase in unstimulated calcineurin activity in the caucasian transplant group compared to the African-American group (*p<0.05 ANOVA, Tukey's post-test). Basal levels of calcineurin activity in African-American transplant patients were the same as in non-transplant patients.

FIG. 23B shows the percent increase in stimulated calcineurin activity was compared for control participants, and caucasian and African-American transplant patients. There was a trend for calcineurin stimulation in the caucasian transplant group to be lower than both control subjects and African-American transplant groups, but the result did not reach significance. Stimulated calcineurin activity in African-American patients was the same as in non-transplant patients (p<0.01 ANOVA, Tukey's post-test).

FIG. 23C shows data shown are plotted in box and whisker format for 32 control subjects who self-identify as caucasian. Anti-CD3/anti-CD28 antibody treatment resulted in a significant increase in calcineurin activity, which was inhibited by both cyclosporine and FK506 (repeated measures ANOVA, Tukey's post-test **p<0.001).

FIG. 23D shows data shown are the results of 44 control subjects who self-identify as African-American plotted in box and whisker format. Anti-CD3/CD28 treatment resulted in a significant increase in calcineurin activity, but neither cyclosporine nor FK506 pre-treatment inhibited calcineurin activity; both groups remain significantly higher than basal and not different from CD3/CD28 stimulated samples (repeated measures ANOVA, Tukey's post-test **p<0.001, *p<0.05).

FIGS. 24A-24D are a series of graphs illustrating T cell cytokine expression correlation with basal and stimulated calcineurin activity. Isolated T cells from a subset of transplant patients (N=6, 3caucasian and 3African-American) were obtained and conditioned media were collected. Production of a panel of cytokines by T cells were measured using Panomics cytokine array (Fremont, Calif.). Luminescence results were quantified by densitometry and normalized to internal controls. Results for individual cytokines were then compared to basal and fold stimulated calcineurin activities for each patient by linear regression. FIGS. 24A and 24B show IL-4 and IL-10 were significantly correlated with basal calcineurin activity (p=0.056 and p<0.05, respectively). FIGS. 24C and 24D show IL-2 and TGFβ were significantly correlated with the fold anti-CD3/CD28 stimulation of calcineurin activity (p<0.05, and p=057, respectively).

FIGS. 25A-25D are a series of graphs illustrating racial differences in TGFβ and IFNγ expression. Plasma TGFβ (FIG. 26A) and IFNγ (FIG. 26B) levels were determined for a subset of control subjects (n=40) and transplant patients (n=34) by ELISA. Data shown are the mean±SEM of duplicate assays. *p<0.05, T-test. Plasma TGFβ (FIG. 26C) and IFNγ (FIG. 26D) levels were determined for caucasian and African-American transplant patients (n=16 and 16, respectively). Data shown are the mean±SEM of duplicate assays. *p<0.05, T-test.

DESCRIPTION OF THE DISCLOSURE

Figure 1:
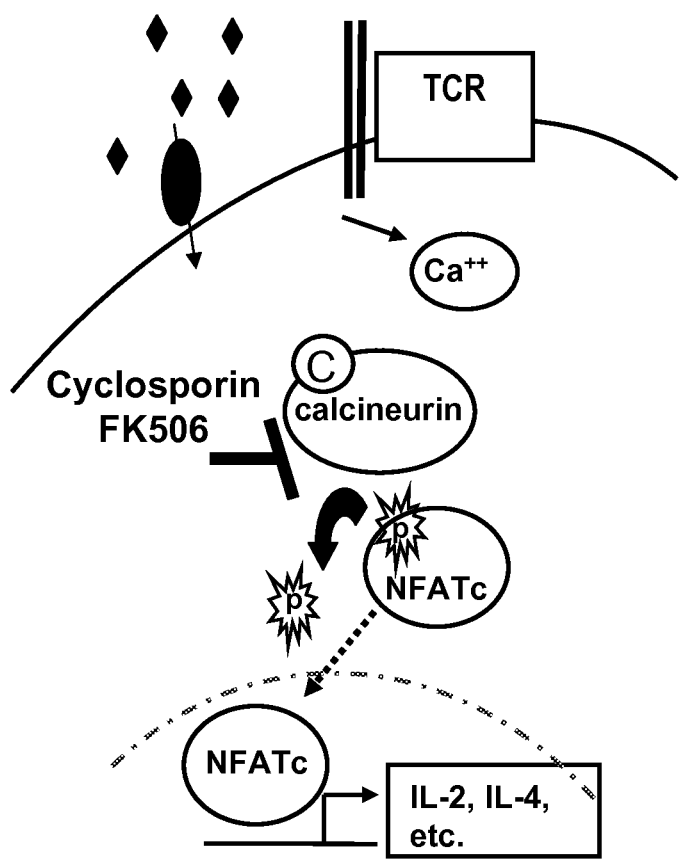
FIG. 1 schematically illustrates calcineurin activation down-stream of the T cell receptor and inhibition by cyclosporine A and FK506 (tacrolimus).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those skilled in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

By "detectably labeled" is meant that a fragment or an oligonucleotide contains a nucleotide that is radioactive, or that is substituted with a fluorophore, or that is substituted with some other molecular species that elicits a physical or chemical response that can be observed or detected by the naked eye or by means of instrumentation such as, without limitation, scintillation counters, colorimeters, UV spectrophotometers and the like. As used herein, a "label" or "tag" refers to a molecule that, when appended by, for example, without limitation, covalent bonding or hybridization, to another molecule, for example, also without limitation, a polynucleotide or polynucleotide fragment provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence, electrochemiluminescence, raman, colorimetric, hybridization protection assay, and mass spectrometry "Peptide" refers to a polymer in which the monomers are amino acid residues which are joined together through amide bonds, alternatively referred to as a polypeptide. A "single polypeptide" is a continuous peptide that constitutes the protein. When the amino acids are alpha-amino acids, either the L-optical isomer or the D-optical isomer can be used, the L-isomers being preferred. Additionally, unnatural amino acids such as beta-alanine, phenylglycine, and homo-arginine are meant to be included. Commonly encountered amino acids which are not gene-encoded can also be used in the present disclosure, although preferred amino acids are those that are encodable. For a general review, see, for example, Spatola, A. F., in Chemistry and Biochemistry of Amino Acids, Peptides and Proteins, B. Weinstein, ed., Marcel Dekker, N.Y., p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. "Amino acids" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference peptide, polypeptide, or polynucleotide, but retains essential properties. A typical variant of a peptide or polypeptide differs in amino acid sequence from another, reference peptide or polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the amino acid sequence of the peptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

The term "peptide-modifying enzyme" as used herein refers to an enzyme that catalyzes the addition or removal of a small-molecule moiety from an amino acid of a protein or peptide. Such an enzyme may be, but not necessarily, capable of recognizing a specific amino acid sequence, thereby allowing the enzyme to attach or delete the moiety from a defined site or sites within the protein or peptide. For example, a protein kinase may add a phosphate group to a protein or peptide and a phosphatase may remove a phosphate group. Calcineurin is known as a calcium ion- and calmodulin-dependent serine-threonine phosphatase and is an element of many intracellular signaling pathways. (Guerini & Klee, (1989) Proc. Natl. Acad. Sci. USA 86:9183-9187). The protein has been identified in eukaryotic cells ranging from yeast to mammals.

The term "kinase" as used herein refers to any enzyme capable of adding a phosphate group to an amino acid sidechain of a protein, polypeptide, or a peptide.

The term "phosphatase" as used herein refers to an enzyme capable of removing a phosphate group from a protein, polypeptide, or a peptide by a hydrolytic reaction.

The term "calcineurin inhibitor" as used herein refers to a compound that in contact with calcineurin either directly or indirectly, reduces or blocks a calcineurin activity, such as, but not limited to, cyclosporine A, tacrolimus (FK506), or derivatives thereof.

The term "target peptide" as used herein refers to a peptide that can function as a substrate for a peptide-modifying enzyme. Such a peptide may comprise an amino acid sequence that is specifically recognized by the enzyme for binding to the peptide and also a site that may receive or have bound thereto a modifying moiety.

The term "to modify the target peptide" as used herein refers to the act of an enzyme adding to, or removing, from a target peptide a small-molecule moiety such as, but not limited to, an acidic moiety.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FRET techniques are well known in the art, and can be readily used to detect the titanium oxide-bound peptides of the present disclosure. See for example U.S. Pat. Nos. 5,668,648, 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

The term "fluorophore" as used herein refers to a fluorescent moiety that in the context of the methods of the disclosure is conjugated to a target peptide or to titanium oxide.

The term "test sample" as used herein refers to any liquid volume added to the reaction mix of the methods of the disclosure, wherein the added liquid volume comprises a known amount of a peptide-modifying enzyme, or may have (suspected) of comprising a peptide-modifying enzyme. A test sample may comprise a known amount of a peptide-modifying enzyme in a buffer suitable for allowing the enzyme to react with a target peptide, or may be derived from a biological sample such as a tissue, cell or fluid sample isolated from a human or animal subject. For example, the test sample can be, but is not limited to, a lysate prepared from isolated cells such as peripheral mononuclear blood cells, a tissue biopsy sample and the like.

The term "Peripheral Mononuclear Blood Cell(s)" as used herein refers to a blood cell having a round nucleus. For example: a lymphocyte, a monocyte or a macrophage. These blood cells are a critical component in the immune system to fight infection and adapt to intruders. The lymphocyte population consists of T cells (CD4 and CD8 positive about 75%), B cells and NK cells (about 25% combined). These cells may be extracted from whole blood using ficoll, a hydrophilic polysaccharide that separates layers of blood, with monocytes and lymphocytes forming a buffy coat under a layer of plasma. This buffy coat contains the PBMCs. PBMC can be extracted from whole blood using a hypotonic lysis which will preferentially lyse red blood cells. This method results in neutrophils and other polymorphonuclear (PMN) cells that are important in innate immune defense to be obtained.

The term "lysate" as used herein refers to a suspension of isolated cells that have had their cell membranes disrupted chemically, physically, enzymatically, or by a combination thereof. The cells may be lysed in a buffer, the disruption in the cell membranes releasing to the surrounding buffer a mix of proteins and other cell constituents. The lysis may be total, where all cells in the treated cell population procedure release their intracellular contents, or partial where at least 50%, advantageously, at least 75%, more advantageously at least 90%, and most advantageously 100% of the cells in a population of isolated cells are disrupted and release their intracellular contents into a suspension buffer.

The term "fluorescently labeled" as used herein refers to conjugating to a peptide substrate a fluorescent moiety, i.e. a fluorophore. A variety of different label moieties are available for use in the substrates of the present disclosure. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes.

The term "selectively detecting" as used herein refers to detecting a wavelength of light from a spectrum of wavelengths. Such selection may be by, for example, filters designed to transmit light of a narrow range of wavelengths while reflecting wavelengths beyond the selected range.

Abbreviations

TAMRA, (tetramethyl-6-carboxyrhodamine); CsA, cyclosporin(e) A; FK506, tacrolimus (FUJIMYCIN™); FRET, Fluorescence Resonant Energy Transfer.

Discussion

Functional Measurements of Calcineurin Activity

Cyclosporine A and tacrolimus alter T cell function by inhibiting the activity of calcineurin (Jorgenson et al., (2003)

Scand. J. Immunol. 57: 93-98; Martinez-Martinez & Redondo (2004) Curr. Med. Chem. 11: 997-1007; Rusnak & Mertz (2000) Physiol. Rev. 80: 1483-1521; Screiber & Crabtree (1992) Immunol. Today 13: 136-142). Calcineurin is a calcium-dependent phosphatase that controls the activity of transcription factors, which then regulate cytokine expression, as schematically shown in FIG. 1. T cells require production of these cytokines in response to various stimuli such as an antigen-presenting cell. Blocking calcineurin activity, therefore, can prevent T cell responses and can result in immunosuppression.

Calcineurin is present in every cell of the body and functions in a variety of important pathways. In the kidney, calcineurin works to regulate production of matrix proteins (Gooch et al., (2001) J. Biol. Chem. 276: 42492-42500; Gooch et al., (2004) J. Biol. Chem. 279: 15561-15570; Gooch et al., (2007) Transplantation 83: 439-447) and in the heart controls hypertrophy (De Windt et al., (2000) Circulation 86: 255-263; Eto et al., (2000) Circulation: 2134-2137; Guo et al., (2002). J. Biol. Chem. 277: 50776-50779; Hayashida et al., (2000) Biochem. Biophys. Res. Comm. 273: 347-351). Loss of these actions likely produces the undesirable side-effects observed with use of calcineurin inhibitors. Accordingly, the degree of calcineurin inhibitor effectiveness in patients should be monitored, preferably by measuring calcineurin activity and correlating calcineurin inhibitor responses thereto.

Although calcineurin has been challenging to measure both in vitro, and especially in vivo, a radioactive assay method (Fruman et al., (1996) Methods in Enzymology 9: 146-154) has been useful in this regard. Data from cells isolated from control subjects not receiving immunosuppressants led to the conclusion that base-line calcineurin activity does not vary significantly with time of day, and that gender had only a minor effect. Data derived from transplant recipient patients, however, was more complex.

First, while tacrolimus levels in transplant recipient patients have not been reported to predict basal calcineurin activity levels in such subjects (Koefoed-Nielsen et al., (2006) Transpl. Int. 19: 821-827; Koefoed-Nielsen & Jorgensen (2002) Transplant. Proc. 34: 1743-1744; Koefoed-Nielsen et al., (2002) Am. J. Transplant. 2: 173-178), several studies do report an apparent correlation between blood cyclosporine A levels and basal calcineurin activity (see, for example, Piccinini et al., (1996) Transplantation 61: 1526-1531; Kung, et al., (2001) Am. J. Transplant. 1: 325-333; Quien et al., (1997) Transplantation 64: 1486-1489). Koefoed-Nielsen et al. proposed a possible resolution to the issue with the finding that cyclosporine A and tacrolimus have different calcineurin activity profiles.

T Cell Receptor Stimulation of Calcineurin is Impaired in Transplant Patients

There has been a failure to identify a significant change in basal calcineurin activity levels between control (non-transplant subjects) and transplant-recipient patients. Embodiments of the present disclosure, however, encompass the approach of detecting and quantifying the response of calcineurin activity levels to T cell receptor stimuli, and correlating this response to the degree of exposure and response of the T cells to immunosuppressants such as, but not limited to, cyclosporine A and tacrolimus.

Figure 2:
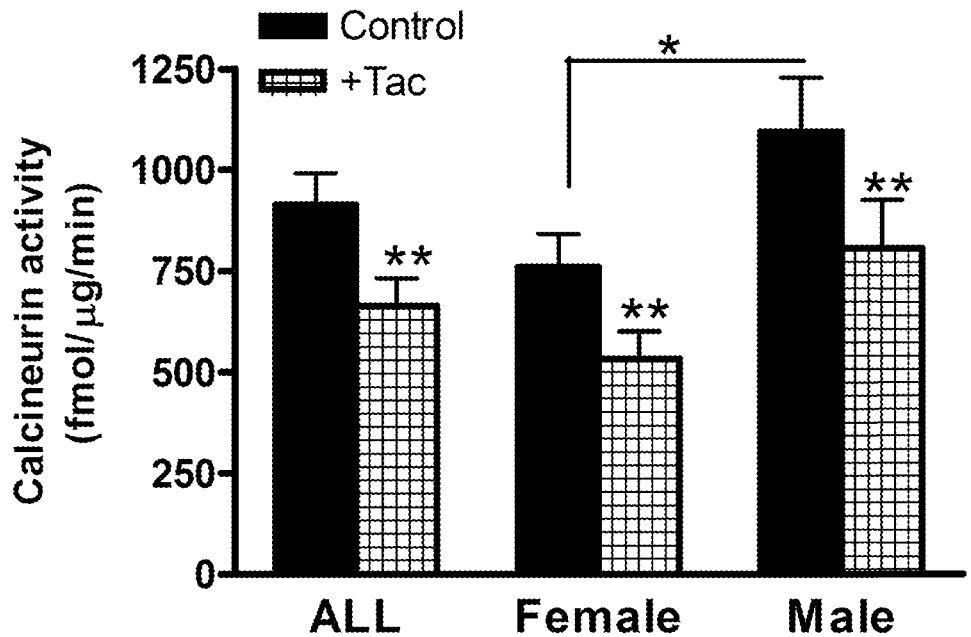
FIG. 2 is a graph illustrating basal and tacrolimus-inhibited calcineurin activity in control cells isolated from subjects not receiving immunosuppressant therapy. T cells were isolated from healthy control subjects (N=81). Samples were then lysed and calcineurin activity measured at baseline and after the in vitro addition of tacrolimus (Tac) (5.0 ng/ml). Data shown in each column are the mean±SE calcineurin activity for each group. Tacrolimus significantly decreased calcineurin activity in the combined group, as well as in female and male subsets ($p<0.001$, Two-way ANOVA). Calcineurin activity in T cells isolated from female controls was significantly lower than males ($p<0.05$, ANOVA, Tukey's post-test).

The addition of calcineurin inhibitors to transplant protocols has markedly reduced acute allograft rejection and prolonged patient survival. Although monitoring of serum immunosuppressant levels has been shown to be a poor indicator of their pharmacological efficacy, there is also little data available concerning calcineurin enzymatic activity in humans and how it is modulated by immunosuppressant therapy. Therefore, basal calcineurin levels in isolated $CD3^+/4^+$ T cells from 81 non-transplant controls and 39 renal allograft patients were measured (using a $^{32}PO_4$-labeled calcineurin-specific substrate). As shown in FIG. 2, a gender difference was observed in the control cohort with activity in males significantly higher than females (1073±134 fmol/µg protein/min versus 758±75 fmol/µg protein/min). Calcineurin activity of both groups was comparably inhibited by 5 ng/ml tacrolimus (27±4% versus 30±4%).

Figure 3:
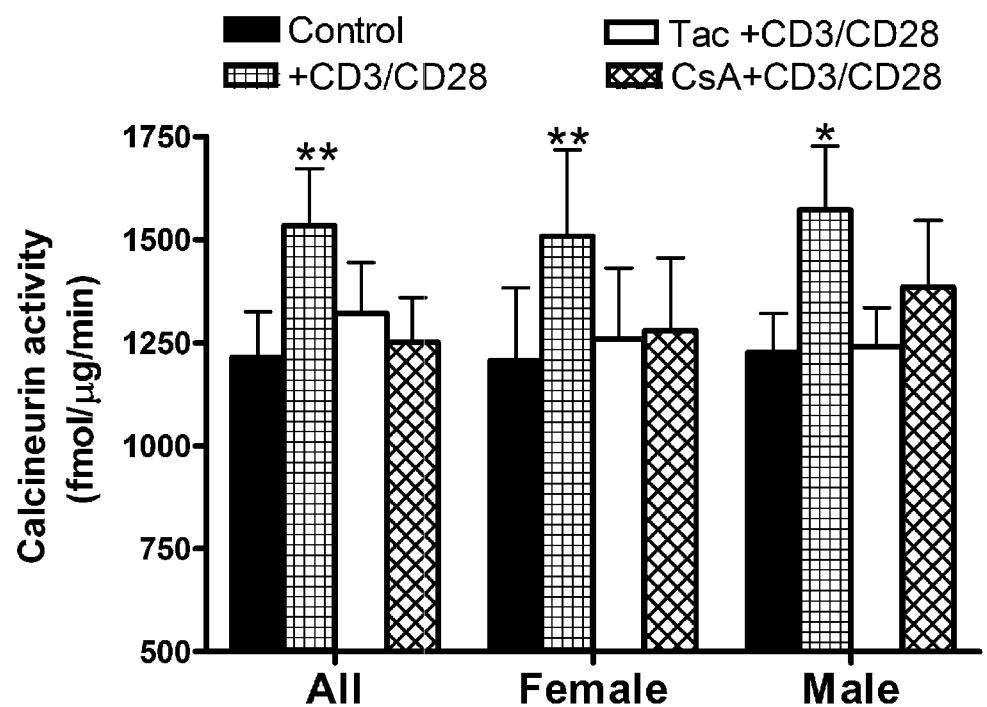
FIG. 3 is a graph illustrating T cell receptor stimulation increases calcineurin activity in normal (controls) cells from subjects not receiving immunosuppressant therapy. T cells isolated from a subset of control subjects (N=30) were separated into 4 aliquots which were then incubated with DMSO (control), anti-CD3/anti-CD28 antibodies (10 μg/ml each), tacrolimus (Tac)+anti-CD3/anti-CD28 antibodies, or cyclosporine A+ anti-CD3/anti-CD28 antibodies. Samples were then lysed and calcineurin activity determined. Data shown are the mean±SE calcineurin activity following each treatment for the combined group, as well as female and male sub-populations. Anti-CD3/anti-CD28 treatment resulted in a significant increase in calcineurin activity and pre-treatment with either tacrolimus or cyclosporine A was effective at blocking the induction (*$p<0.05$, **$p<0.01$, Two-way ANOVA). There was no gender differences in stimulated calcineurin activity or in inhibition by tacrolimus or cyclosporine A.

The effects of cyclosporine A and tacrolimus on calcineurin activity in $CD3^+/4^+$ T cells isolated from normal controls and renal transplant patients were examined, as shown in FIG. 3. It was shown that post-transplant immunosuppression can lead to changes in calcineurin activity in response to TCR stimulation. Since calcineurin is a downstream target of the T cell receptor (TCR), activity was measured in isolated T cells following incubation with anti-CD3/anti-CD28 antibodies to stimulate the TCR. Calcineurin activity increased significantly from 1214±111 fmol/µg protein/min to 1652±138 fmol/µg protein/min; addition of either tacrolimus or cyclosporine A (500 ng/ml) blocked the CD3/CD28 stimulation, as shown in FIG. 3.

Figure 4:
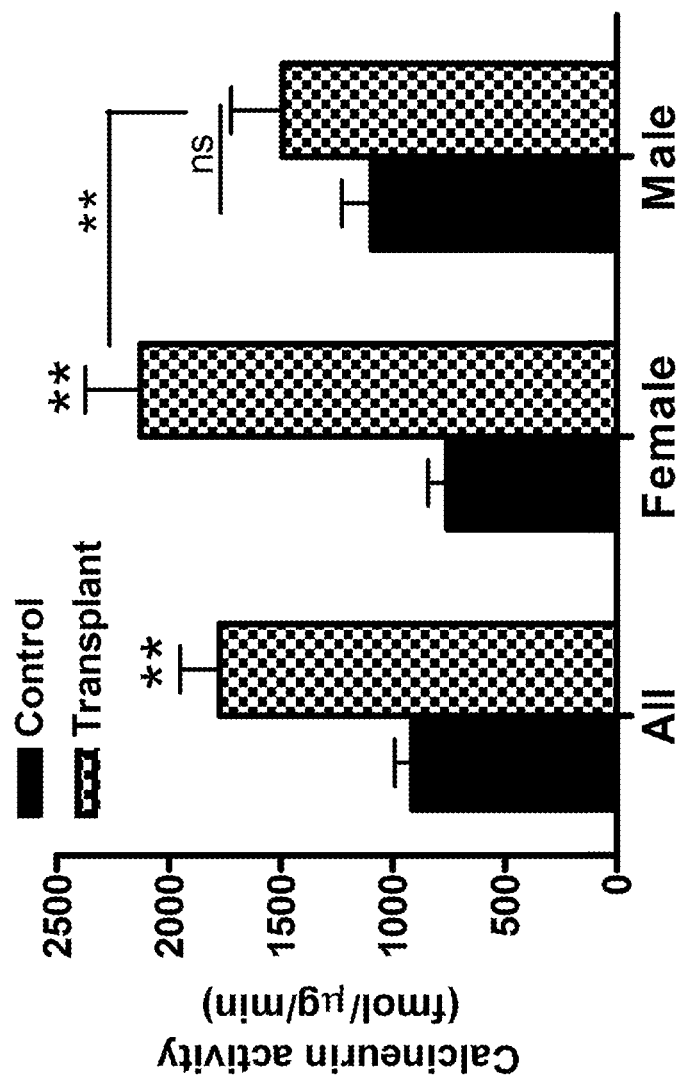
FIG. 4 is a graph illustrating increased basal calcineurin activity in T cells isolated from 39 post-renal transplant subjects (and therefore exposed to immunosuppressants). Data shown are the mean±SE calcineurin activities of controls and transplants, as well as female and male subsets of each cohort. Basal calcineurin activity was significantly higher in transplant subjects as a whole and in the female subset (**$p<0.01$, Two-way ANOVA). Male allograft recipients had lower calcineurin activity compared to females (*$p<0.05$, ANOVA, Tukey's post-test).
Figure 5:
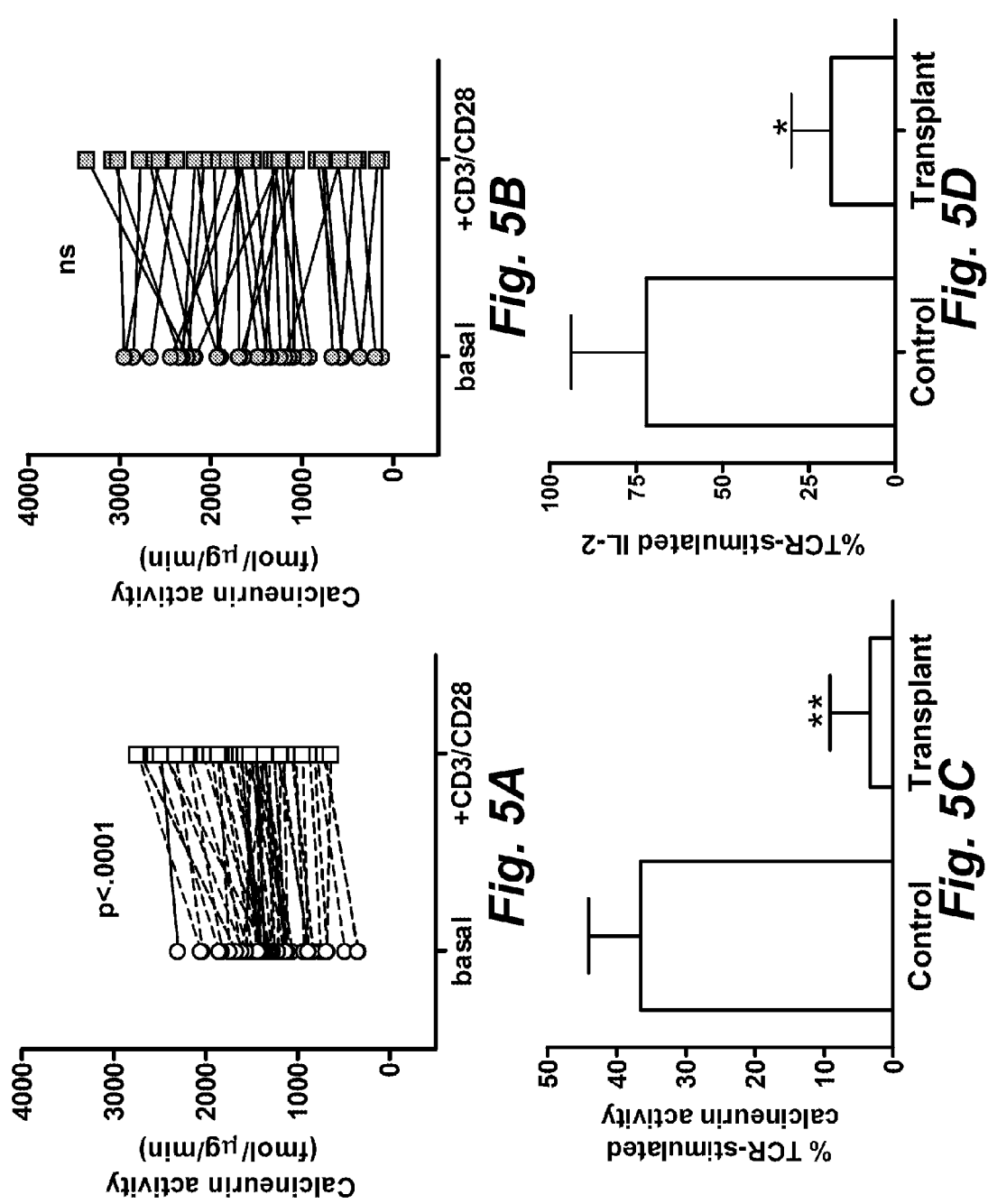
FIGS. 5A-5D are a series of graphs illustrating calcineurin activity in T cells isolated from transplant subjects is not increased in response to T cell receptor stimulation.
Figure 6:
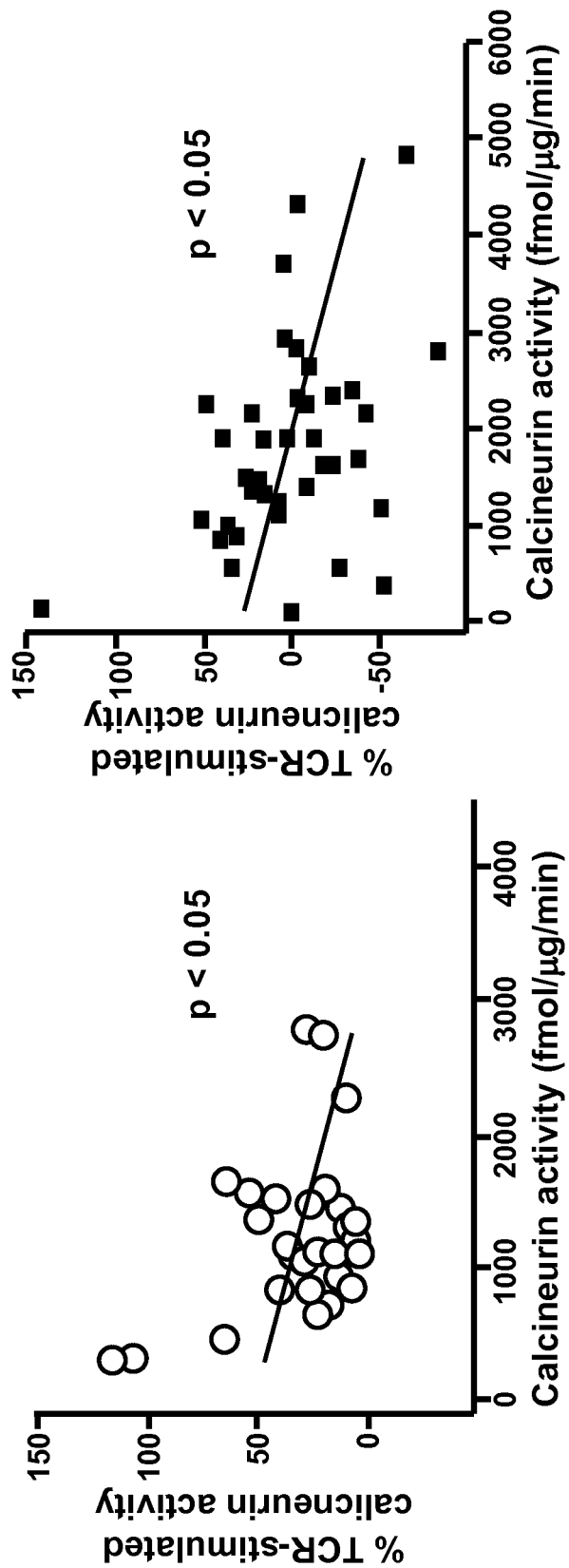
FIGS. 6A and 6B are graphs illustrating basal and T cell receptor-stimulated calcineurin activity are inversely related. Basal calcineurin activity and anti-CD3/anti-CD28 antibody-stimulated activity were compared. There is a statistically significant inverse relationship between basal calcineurin activity and the percent stimulation in response to T cell receptor stimulation in both the control (FIG. 6A) and transplant (FIG. 6B) groups ($r^2$ 0.136, p<0.01 and $r^2$ 0.154, p<0.05 respectively, linear regression).
Figure 7:
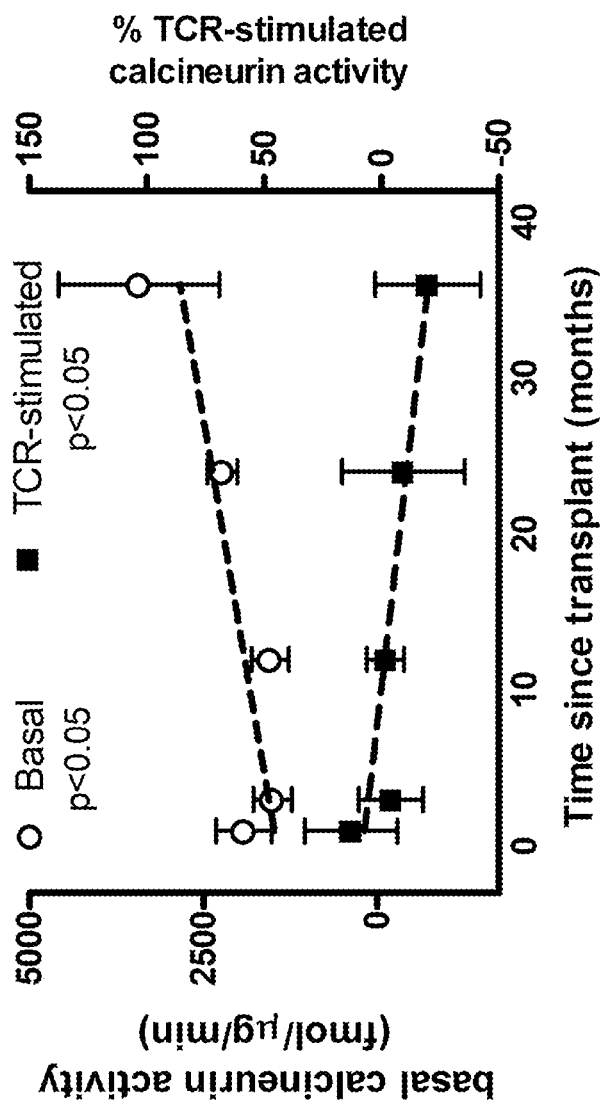
FIG. 7 is a graph illustrating the correlation between basal calcineurin activity and the time since renal transplantation. Basal calcineurin activity and the response to TCR stimulation were compared in renal allograft recipients and grouped by time since transplantation. Calcineurin activity in patients 1-2 months post-transplant was compared with patients of 3, 12, 24, and 36 months transplant duration. There was a significant positive correlation between basal calcineurin activity and duration of transplantation (p<0.05) and a significant inverse correlation between response to T cell receptor stimulation and duration of transplantation (p<0.05).

With therapeutic levels of tacrolimus and cyclosporine A administered to a transplant subject (mean 11.4 and 172 ng/ml), basal calcineurin activity was higher among renal transplant recipients than among controls (1776±175 fmol/µg protein/min versus 914±78 fmol/µg protein/min), as shown in FIG. 4 and compared to the control results in FIG. 2. In contrast to the results with control cells that had not been previously exposed to a calcineurin inhibitor (FIG. 5A), anti-CD3/anti-CD28 antibodies failed to stimulate calcineurin activity in T cells derived from transplant subjects (FIG. 5B). Also, basal and stimulated calcineurin activities are inversely related (FIGS. 6A and 6B). Consistent with this finding, basal activity in resting T cells rose over time post-transplant while stimulation fell ($r^2=0.785$, $p<0.05$) (FIG. 7). These data indicate that the determinations of TCR-stimulated calcineurin activity following renal transplantation provides an indicator for monitoring the extent or progress of immunosuppression of individual patients.

To use calcineurin activity determinations as indicators of the efficacy of immunosuppressant drugs, it is necessary to first identify reproducible differences in calcineurin activity levels or inducible changes in calcineurin levels between control cells and cells derived from a transplant population subject to immunosuppressant therapeutic agents. No aspect of calcineurin activity had been shown to be consistently altered with cyclosporine A or tacrolimus therapy. The present disclosure, however, encompasses use of a calcineurin-dependent activity that can be significantly and clearly modulated in transplant patients.

Figure 8:
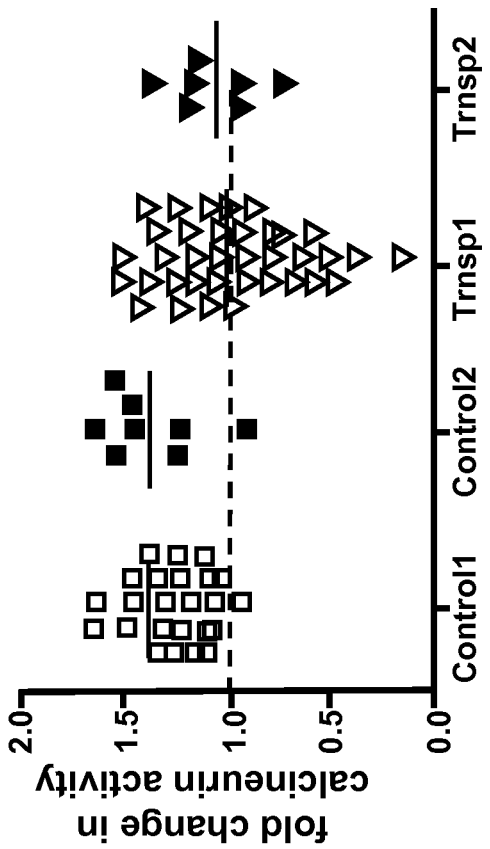
FIG. 8 is a graph illustrating the calcineurin activity level following CD3 stimulation/CD28 co-stimulation, and using a fluorimetric calcineurin assay method.

Basal calcineurin activity in isolated T cells of transplant patients is increased compared to enzyme activity levels seen in control T cells, as shown in FIG. 4. While there is a degree of overlap between the two groups, as illustrated in FIG. 8, the finding suggests that the primary observable change in calcineurin activity with chronic cyclosporine A or tacrolimus treatment is not a sustained decrease in basal levels of the enzyme.

Stimulation of the TCR in T cells from transplant patients receiving therapeutic blood levels of tacrolimus or cyclosporine A did not significantly increase calcineurin activity above basal levels. However, enzyme activity in normal PBMC controls increased by roughly 40% (FIGS. 8 and 9), indicating that a TCR-stimulated calcineurin level (or lack thereof)

could be a more sensitive indicator of in vivo calcineurin inhibitor functionality than the basal levels of enzyme activity.

As shown in FIGS. 10A and 10B, The decrease in TCR-stimulated calcineurin activity in parallel with an increase in the basal activity in PBMCs of transplant subjects suggested a relationship between basal enzyme activity and TCR stimulation. In control and transplant PBMC cohorts, an inverse relationship was identified. While not wishing to be bound by any one theory, increased basal calcineurin activity as seen in PBMCs of transplant patients could be a compensatory response to loss of TCR stimulation. In a chronic setting, drugs such as cyclosporine A and tacrolimus act preferentially to inhibit acute activation of calcineurin rather than reduce steady-state baseline levels. Alternatively, immune challenges such as an organ transplant may provoke a chronic elevation in T cell activation and, consequently, of calcineurin activity. Acute challenge of the TCR (such as exposing PBMCs of transplant patients to an anti-CD3 antibody) may then produce no additional increase. Thus, FIGS. 5A and 5B show that only 10% of control PBMC samples had basal calcineurin activity levels greater than 1700 fmol/μg protein/min, whereas almost half of transplant recipient PBMC samples had basal calcineurin activity levels greater than 1700 fmol/μg protein/min.

Supporting the possibility that TCR-stimulation of calcineurin may be physiologically relevant in transplant populations, there was a statistically significant correlation between the duration of transplantation and calcineurin activity. Basal calcineurin activity gradually declined and TCR-stimulation increased in subsets of allograft recipients that were 1, 2, and 3 years post-transplant, consistent with gradually declining immune activation and increased graft stability.

Figure 9:
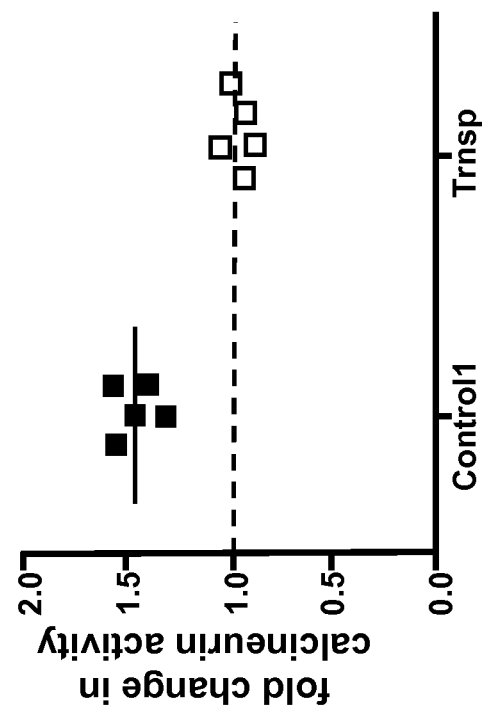
FIG. 9 is a graph illustrating changes in calcineurin activity following T cell CD3-only stimulation and using a FRET-based fluorimetric calcineurin assay method. The fold difference between untreated and treated samples is shown. All 5 control samples tested responded with an increase in calcineurin activity. There was no response seen in transplanted subjects.

Since calcineurin is an integral signaling mediator of most cells, activation of calcineurin in response to a non-cell specific stimuli-PMA was also examined. To further investigate specific activation of calcineurin downstream of the TCR, samples were treated with anti-CD3 antibodies only. PBMC samples were obtained and the basal and TCR-stimulated calcineurin activities thereof were examined, as shown in FIG. 9. It was found, as shown in FIG. 9, that by only stimulating the cells with anti-CD3 antibody (and using the FRET-based assay) that the was a more highly resolved distinction between control and transplant T cells than if co-stimulation was also applied.

The optimal treatment doses and TCR-stimulation times were determined for phorbyl myristolic acid (PMA) and anti-CD3 antibodies by both dose and time courses. The data in FIGS. 10A-10D show that there is no significant difference in basal calcineurin activity between control PBMCs and transplant patient PBMCs (FIGS. 10A and 10B). Both the mean and distribution of calcineurin activities were similar.

It was shown that PMA stimulated calcineurin activity in control cells, but not in the transplant recipient-derived PBMC samples. Similarly, TCR-specific activation by anti-CD3 was observed only in control PBMCs, and the stimulated calcineurin activity level was statistically lower in the transplant-related PBMC group (FIG. 10C).

It was also shown that the fold change in calcineurin activity in response to anti-CD3 was sensitive to tacrolimus inhibition. Thus, PBMCs from control subjects were incubated with increasing amounts of tacrolimus before the anti-CD3 stimulation and the calcineurin activity was then measured. FIG. 10D shows that the fold change in calcineurin with anti-CD3 stimulation was inhibited by tacrolimus in a dose-dependent fashion.

It was further determined whether in vitro addition of calcineurin inhibitors could further inhibit calcineurin activity in samples from transplant subjects. Although FIG. 10D shows that calcineurin inhibitor complexes remain intact through the isolation, lysis, and assay processes, the effects of in vivo calcineurin inhibitors influencing in vitro calcineurin activity was investigated. PBMCs isolated from subjects not receiving calcineurin inhibitors such as cyclosporine A or tacrolimus (i.e., pre-transplant controls) were in vitro-treated with cyclosporine A or tacrolimus and the percentage inhibition of basal calcineurin activity was determined.

Figure 11A:
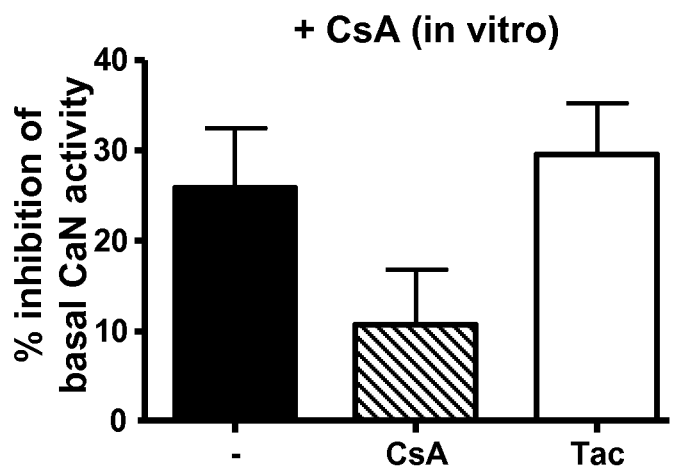
FIGS. 11A and 11B are a pair of graphs showing the in vitro effect of calcineurin inhibitors. Inhibition of basal calcineurin activity by in vitro incubation with calcineurin inhibitors was assessed in: (a) subjects not receiving any inhibitor, i.e., the control; (b) subjects on cyclosporine A, and (c) subjects on tacrolimus. PBMCs isolated from each group were then treated with cyclosporine A (FIG. 11A), or tacrolimus (FIG. 11B) in vitro and calcineurin activity levels determined. Patients already taking cyclosporine A demonstrated the least response to additional in vitro cyclosporine A treatment. The mean response of patients taking tacrolimus was not different from controls or patients on cyclosporine A, but there was a trend toward two response groups within the cohort. Approximately half had little or no inhibition by tacrolimus whereas the other half were inhibited to a greater degree (FIG. 11B, inset).

Cyclosporine A decreased basal calcineurin activity in control PBMC samples by approximately 25%. However, cells isolated from patients already receiving cyclosporine A (having received a transplant) demonstrated only about a 10% reduction in basal activity, while the response of such cells to tacrolimus was similar to that of the control cells, as shown in FIG. 11A.

Figure 11B:
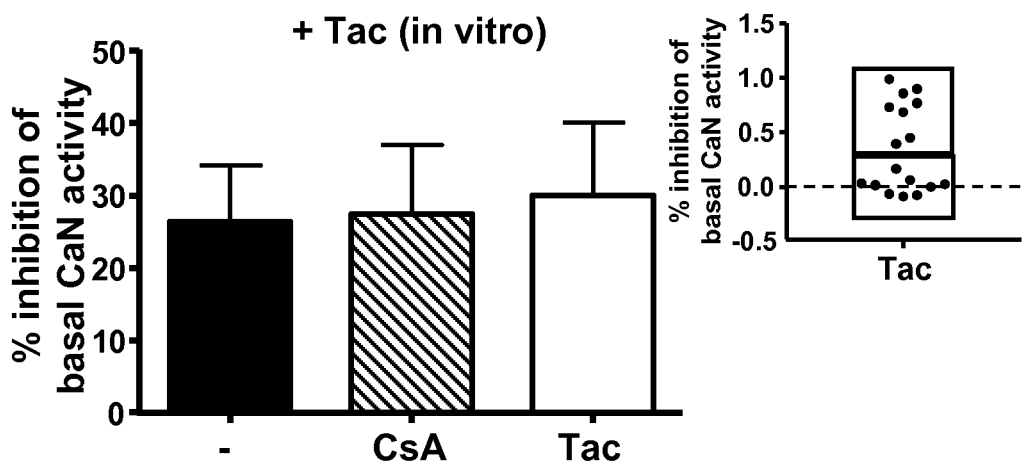
Figures 12A, 12B:
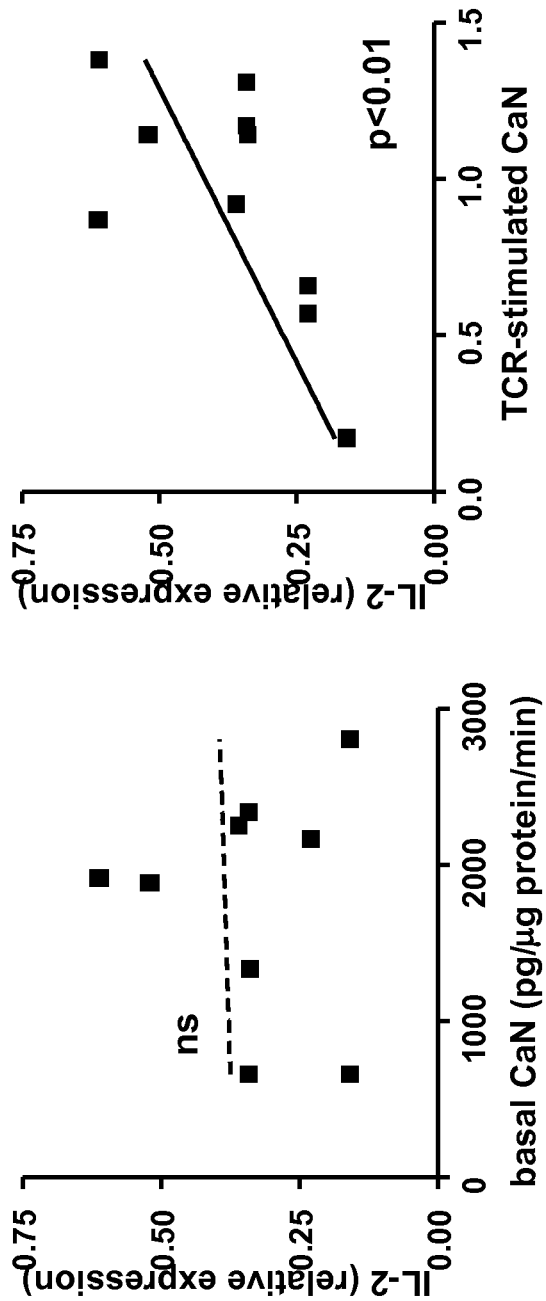
FIGS. 12A and 12B are a pair of graphs illustrating that IL-2 production is associated with TCR-stimulation of calcineurin.

In contrast, PBMCs derived from patients currently on tacrolimus could still be inhibited by cyclosporine A, and by a comparable degree to the control cells (FIG. 11B). The mean inhibition of the group by in vitro tacrolimus was also similar to that seen in control PBMCs. Closer examination of individual responses, however, revealed a bi-phasic response with one group of patients showing almost no additional inhibition, and the other group a substantially higher level of inhibition (FIG. 11B; inset). Also, calcineurin stimulation was compared with production of cytokines in a subset of the transplant subjects with IL-2 production corresponded to stimulated calcineurin (FIG. 12B), but not basal calcineurin activity (FIG. 12A).

Predictive Assay for Assessing Patient's Response to Transplantation and Immunosuppression Therapies Calcineurin inhibitors have been a cornerstone of post-transplant immune suppressing regiments for over 2 decades. During that time, short-term survival rates have improved remarkably. Current treatment strategies, however, are not yet sufficient to improve long-term outcomes to a similar degree. Variability in response to calcineurin inhibitors may be an important part of therapeutic limitations. While dose ranges have been generally established, it has long been known that there is little correlation between blood level of calcineurin inhibitor and rejection, or the development of complications including nephrotoxicity. In addition, it is apparent that even with optimal calcineurin management, some individuals such as African Americans remain at higher risk for rejection. While there has been considerable effort to identify factors that may contribute to differences in racial disparities post-transplantation, no combination of societal or medical factors appears to completely answer the question. One factor that may explain both the lack of correlation between therapeutic levels and outcome, as well as the relatively higher risk of some patient populations, appear to be differences in the enzymatic response of calcineurin to pharmacological inhibitors.

There is a striking difference in calcineurin inhibitor efficacy in Caucasian (caucasian) and African American (African-American) study participants. African-American control subjects are resistant to both cyclosporine- and FK506-mediated inhibition of calcineurin activity and African-American transplant recipients continued to respond normally to T cell stimuli despite having received therapeutic levels of FK506 and cyclosporine.

The data indicate multiple and distinct actions of the calcineurin enzyme. There were changes in both the basal levels and the degree of calcineurin stimulation and both activities are modulated by transplantation and race. For example, transplant patients as a whole have significantly higher basal levels of calcineurin (1811±174 pg/µg protein/min versus 1133±103 pg/µg protein/min, p<0.05). Considering that all transplant patients were currently receiving standard immunosuppressant regiments including calcineurin inhibitors, this result was surprising.

Likewise, race appears to correlate with calcineurin activity. Caucasian transplant patients had significantly higher basal calcineurin levels and caucasian control subjects had slightly higher calcineurin levels than did African-American control subjects (although not statistically significant).

There was a stronger effect of calcineurin inhibitors on stimulation of T cell calcineurin. As a group, calcineurin response to anti-CD3/anti-CD28 co-stimulation in transplant patients was significantly less than that of the control subjects (8% versus 41%), indicating that the main effect of immune suppression is the result of blocking stimulation of calcineurin as opposed to calcineurin activity as a whole. It is therefore highly significant that this is the aspect of calcineurin activity that is the most affected by race.

African-American control patients were resistant to FK506- and cyclosporine-mediated inhibition of anti-CD3/anti-CD28 co-stimulation. It is also of interest to note that there is a significant correlation between the degree of cyclosporine A-mediated inhibition and FK506-mediated inhibition in both caucasian and African-American control subjects, as shown in Table 1, suggesting that lack of calcineurin inhibition is not specific to the mechanism of action of either drug.

affects of pre-transplant diagnoses (for example, diabetic transplant patients had, in general, lower basal calcineurin activity than patients with other diagnoses) race consistently correlated with lower basal levels and higher stimulated calcineurin activity independent of diagnoses.

Linear regression analyses of T cell cytokine production and basal and stimulated calcineurin activities resulted in a novel finding that different aspects of calcineurin correlate with changes in different cytokines. More specifically, basal calcineurin activity correlated with levels of the Th2 cytokines IL-10 and IL-4 while stimulated calcineurin correlated with TGFβ and IL-2, both Th1 cytokines, as shown in FIGS. 24A-24D.

The data show that caucasian transplant patients have the combined "profile" of high basal calcineurin and low stimulated calcineurin. If those patterns are applied to results of our cytokine study, the outcome would be high levels of anti-inflammatory Th2 cytokines and low levels of pro-fibrotic, Th1 cytokine. In contrast, African-American patients continue to have high levels of stimulated calcineurin activity despite therapeutic levels of calcineurin inhibitors and lower basal levels of calcineurin compared to caucasian patients. This translates to low levels of Th2 cytokines and high levels of Th1. It is likely, therefore, that racial differences in calcineurin enzymatic activity may underlie at least some disparities in clinical outcomes.

It is shown, therefore, that there is a racial distinction in the effectiveness of calcineurin inhibitors to block T cell stimulation of calcineurin activity. Importantly, changes in stimu-

TABLE 1

Multi-variate analysis of control participants by race

|  | Basal | | FK5/basal | | Fold Stim. | | FK5/CD3 | | CsA/CD3 | |
| --- | --- | --- | --- | --- | --- | --- | --- | --- | --- | --- |
|  | CC[a] | AA[b] | CC | AA | CC | AA | CC | AA | CC | AA |
| Race |  |  |  |  |  |  |  |  |  |  |
| Age | p = 09 | ns | ns | ns | ns | ns | ns | ns | ns | ns |
| BMI | ns | ns | p = .0 | ns | p < .01 | ns | ns | ns | ns | ns |
| WBC | ns | ns | ns | p = .01 | ns | ns | ns | p~09 | ns | p = 0 |
| Lymphs | ns | ns | ns | p = .01 | ns | ns | ns | p = .0I | ns | ns |
| Gender | ns | ns | ns | ns | ns | ns | ns | ns | ns | ns |
| FK5/basal | ns | ns |  |  |  |  |  |  |  |  |
| Fold stimulation | ns | p=<. | ns | ns |  |  |  |  |  |  |
| FK5/CD3 | ns | p < .0 | ns | ns | ns | ns |  |  |  |  |
| CsA/CD3 | ns | p = 06 | ns | p = .12 | ns | ns | p = 08 | p < 01 |  |  |

[a]CC: Caucasian
[b]AA: African-American

In evaluating the data, elevated levels of basal activity in caucasian transplant patients reflected a maximal activity, thereby providing an explanation for decreased stimulation in this group. However, linear regression analyses indicated no significant correlation between basal and stimulated calcineurin activities for either the transplant group or the control subjects. There was no significant correlation between basal and stimulated calcineurin activity in either caucasian or African-American controls (Table 1).

Additional factors were examined to determine if other differences between caucasian and African-American patients could account for the changes observed. For example, African-American patients in our study cohort were more likely to have received a transplanted organ from a deceased donor compared to caucasian patients. However, there was no difference between basal and stimulated activities of calcineurin of caucasians receiving living-donor kidneys and deceased-donor kidneys, indicating that the donor source does not account for differences in basal and stimulated calcineurin activity. Similarly, while there were some lated calcineurin activity correlate with regulation of pro-fibrotic cytokines. Together, these data provide a new mechanism for racial disparities in long-term survival following organ transplantation.

Calcineurin Assays

The fluorimetric-based assay methods of the disclosure provide a target substrate such as, but not limited to, a peptide that has a first fluorophore conjugated thereto. When it is desired to detect or measure the activity of a peptide modifying enzyme in a sample, a peptide is obtained that has an amino acid sequence specifically recognized by the enzyme, for example a phosphatase, under the conditions of the assay. To detect a phosphatase activity, the target peptide is further phosphorylated at a site within the peptide that is selectively recognized by the phosphatase when phosphorylated.

In embodiments of the assays of the disclosure, therefore, the labeled phosphorylated peptide substrate is allowed to react with a test sample under conditions that allow for calcineurin activity. A mixture of dephosphorylated and phosphorylated peptide will then result. The dephosphorylated peptide and the phosphorylated peptide substrate can be partitioned by contacting with a titanium oxide matrix that specifically binds the phosphorylated peptide under acidic conditions.

The present disclosure provides methods for determining the level of activity of the calcineurin in a biological sample derived from a human or animal patient. Embodiments of the assays may be used to determine the response of the calcineurin activity of a patient to a calcineurin inhibitor, which provides predictors for the outcome of transplantation and/or immunosuppression treatment. Information from the response of the enzyme to a potential inhibitor may further direct the physician to adjust a regimen of therapeutic agents that may increase the acceptance of the patient towards a transplanted organ, and reduce rejection thereof.

The methods of the present disclosure allow for the assaying of the calcineurin activity by a conventional assay based on measuring the release of a radioactive phosphorus label from a peptide substrate, or by using a fluorescence-based assay that detects a phosphorylated target peptide detectably labeled with a fluorophore that provides several practical advantages over to the more traditional assay.

(a) Radioassay of Calcineurin Activity

Calcineurin is a calcium-dependent, serine/threonine phosphatase distinct among phosphatases because its activity requires calcium and is not sensitive to inhibition by compounds that block the related phosphatases PP1A and PP2A. Therefore, the most common methods to measure calcineurin activity rely on calcium-dependent dephosphorylation of a substrate derived from the RII subunit of protein kinase A in the presence of PP1A/PP2A inhibitors.

In an established assay method for calcineurin activity (Fruman et al., (1996) *Methods in Enzymology* 9: 146-154; Lea et al., (2002) *J. Am. Soc. Nephrol.* 13: 1750-1756 incorporated herein by reference in their entireties), a peptide substrate is incubated with protein kinase A and $^{32}$Py[ATP] under appropriate conditions to phosphorylate the peptide with a radioactive residue. The labeled substrate is then purified and used within a short period of time as a substrate for calcineurin. To measure calcineurin activity, equal parts of cell lysate, reaction mixture, and labeled substrate are incubated at about 30° C. for about 10 minutes before the reaction is terminated. To determine how much of the phosphorylated peptide has been dephosphorylated, a column is prepared for each reaction containing pre-charged ion-exchange resin. A reaction mix is loaded on the column and unincorporated phosphate, which does not bind the resin, is eluted. The amount of radioactivity in the eluted fractions is then measured in a scintillation counter and used to quantify calcineurin activity. In general, the method has several drawbacks including the use of radioactive phosphate for labeling of the peptide substrate, background due to unincorporated phosphate, reliance upon ion exchange to separate phosphorylated from non-phosphorylated peptide, and the final measurement of free phosphate to represent calcineurin activity. These factors increase variability of the data and reduce reproducibility of the assay.

(b) Non-FRET-Based Fluorescence-Based Calcineurin Assay

Figure 13:
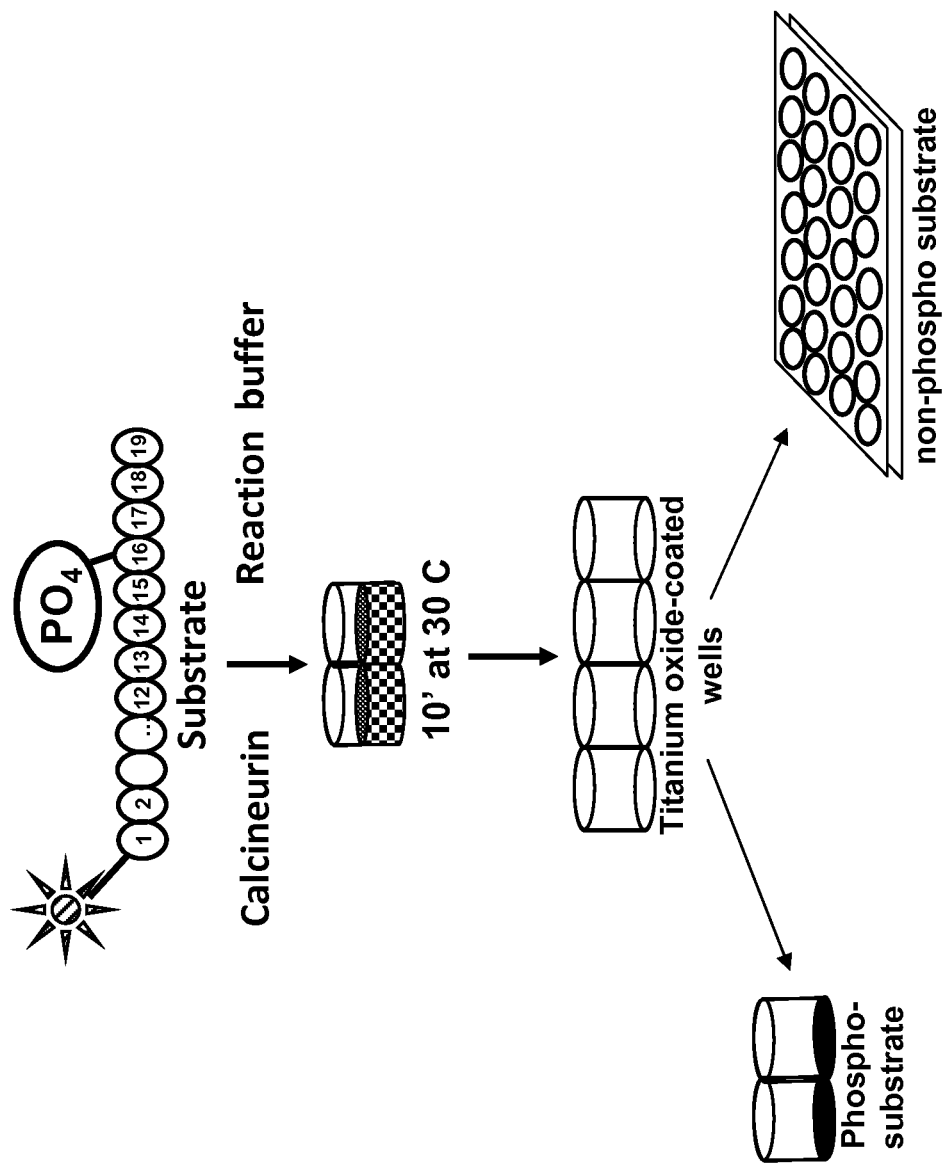
FIG. 13 illustrates a schematic of a fluorimetric calcineurin assay. The RII peptide substrate is synthesized with a phosphoserine 15 residue and conjugated to an amino-terminus fluorescent tag. In a 96-well plate, the labeled substrate is mixed in equal parts with reaction buffer and sample and allowed to incubate at about 30° C. for about 10 minutes. Each well is then transferred to a 96-well plate coated with titanium-oxide followed by gentle shaking to allow binding of phosphorylated substrate. Finally, the contents of each well are moved to a new 96-well plate and the amount of dephosphorylated peptide determined by fluorimetry at 485 nm excitation and 528 nm emission.

Embodiments of the disclosure may incorporate a fluorescence-based assay to determine calcineurin activity using well-characterized reaction conditions, a fluorescently labeled phosphopeptide substrate, and separation of dephosphorylated substrate by titanium oxide, as schematically shown in FIG. 13. The fluorescence-based methods according to the present disclosure are rapid, involve no radioactivity, and are suitable for high-throughput assays, and automated assay systems. Furthermore, with the use of a standard curve, precise measurements of calcineurin activity are attainable.

In brief, a peptide is synthesized that can be phosphorylated at the Ser-15 position during peptide synthesis itself, thereby eliminating the need for enzymatic labeling. In embodiments of the methods according to the present disclosure, the peptide may have, but is not limited to, the RII peptide amino acid sequence NH$_2$-DLDVPIPGRFDRRVS-VAfrican-AmericanE-COOH (SEQ ID NO.: 1). Fluoresceinyl-DLDVPIPGRFDRRVSVAfrican-AmericanE, and its phosphorylated analog (Fluoresceinyl-DLDVPIPGR-FDRRVpSVAfrican-AmericanE where pS=L-phosphoserine) are variants of the peptide SEQ ID NO.: 1 for use in the methods of the disclosure, and in particular for the detection of calcineurin activity.

It is contemplated that the sequence may be such as to be capable of distinguishing isoforms of a phosphatase. For example, the substrate peptide may have, but is not limited to, the amino acid sequence according to SEQ ID NO.: 1 or 2, wherein the peptides can serve as specific substrates for the phosphatase calcineurin, and wherein SEQ ID NO.: 2 is specific for one isoform of calcineurin, but not others.

The peptide can be detectably labeled with a fluorescent moiety at its amino-terminus, the fluorescent label being, but not limited to, fluorescein or TAMRA. Next, the tagged, labeled peptide can be incubated with the desired lysate for about 10 minutes at about 30° C.

The methods of the present disclosure make use of the property that titanium oxide is highly specific for binding of phosphorylated peptides to separate phosphorylated from non-phosphorylated peptide. To this end, plates coated with titanium oxide are utilized. Reaction mixes are transferred to the titanium oxide plate, followed by gentle shaking at room temperature for 5 minutes to allow binding of the phosphorylated peptide. Dephosphorylated peptide, which does not bind to the titanium oxide matrix, can then be transferred to a new plate and quantified by fluorimetry of the fluorescein tag.

Figure 14A:
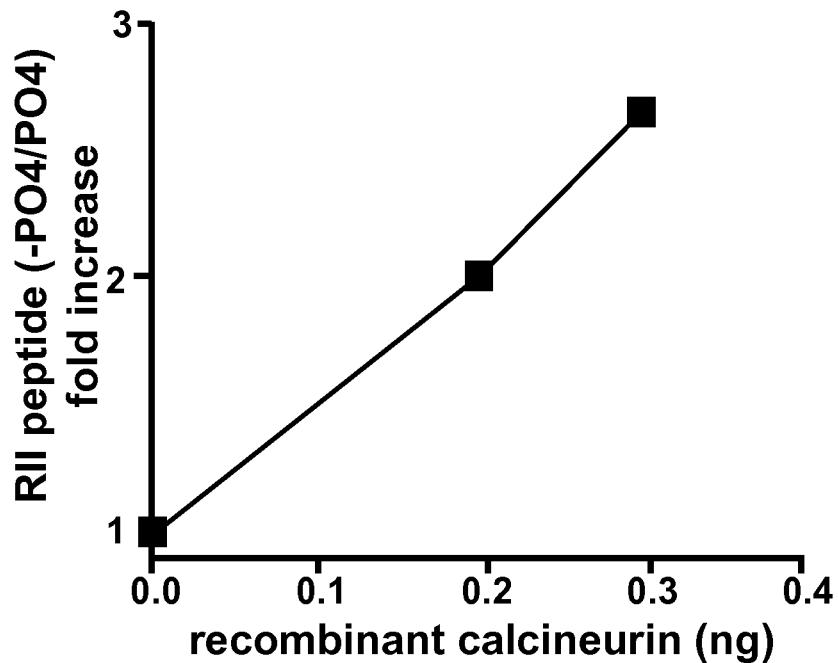
FIGS. 14A and 14B show the validation of fluorescein-labeled RII peptide by mass spectrometry.
Figure 14B:
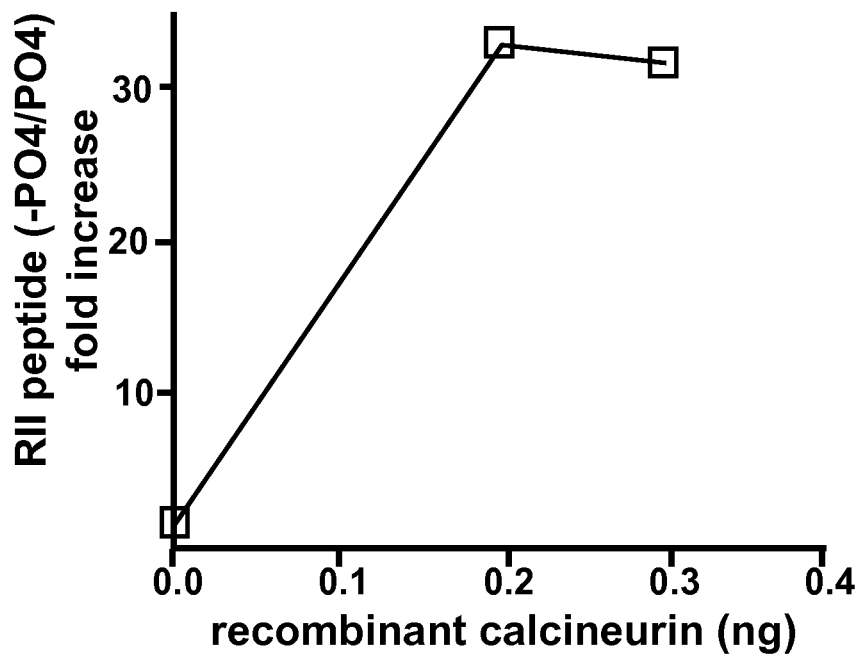

To validate this method, mass spectrometry was used to verify that the labeled, tagged peptide can be dephosphorylated by calcineurin. Phosphorylated, fluorescein-tagged peptide was used as a substrate for calcineurin under established reaction conditions. After stopping the reaction with 0.1% acetic acid in 10% acetonitrile, the samples were analyzed by mass spectrometry. FIG. 14A shows that recombinant calcineurin stimulated a dose-responsive increase in the relative amount of dephosphorylated to phosphorylated peptide. Also titanium oxide matrix effectively separates dephosphorylated from phosphorylated peptide. The reactions generating the data FIG. 14A were performed identically to those for FIG. 14B, but with the additional step of incubating the reactions in titanium oxide-coated wells for 5 minutes. The amount of dephosphorylated peptide in the unbound fraction was analyzed by mass spectrometry. FIG. 14B shows that there was a 30-fold increase in the amount of dephosphorylated peptide in the unbound fraction with the addition of recombinant calcineurin.

Figure 15A:
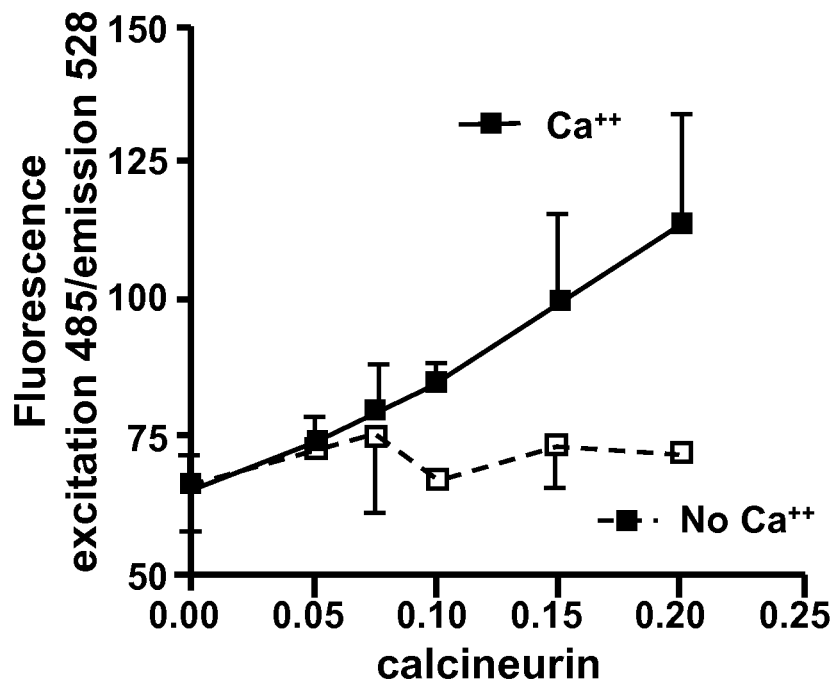
FIGS. 15A and 15B are graphs illustrating dose-responses of non-FRET-based fluorescent calcineurin assays with recombinant calcineurin.

After confirming that the labeled peptide could be dephosphorylated, and the titanium oxide effectively separated phosphorylated from non-phosphorylated peptide, the assay was characterized. Reactions containing increasing amounts of recombinant calcineurin in either normal reaction buffer or calcium-free reaction buffer were analyzed. Calcineurin in normal buffer resulted in dephosphorylation of the peptide in a dose-dependent manner. In the absence of calcium, however, there was no increase in dephosphorylation, as shown in FIG. 15A.

Figure 15B:
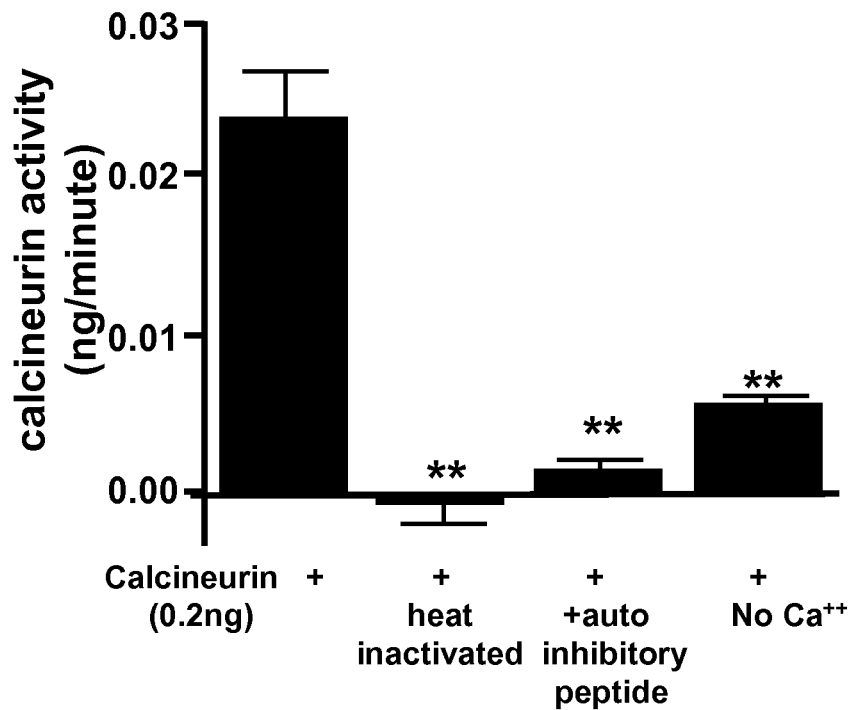

Reactions using 0.2 ng of recombinant calcineurin along with standard controls for calcineurin activity, including heat inactivation of the recombinant enzyme, addition of an auto-inhibitory peptide, absence of calcium, and chelation of calcium with EGTA were investigated. Dephosphorylation by 0.2 ng calcineurin was significantly reduced (ANOVA) by each of these conditions, as shown in FIG. 15B.

Figure 16A:
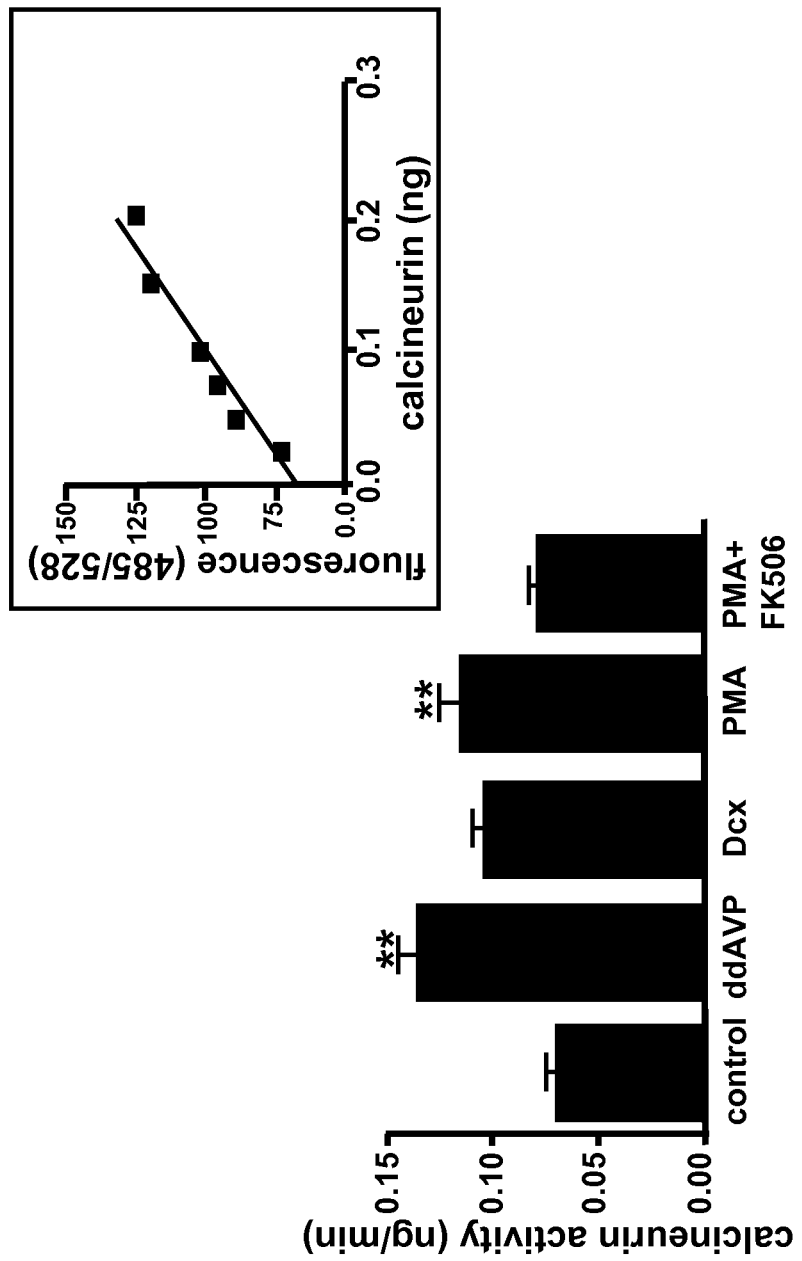
FIGS. 16A-16B are graphs illustrating the detection of calcineurin-mediated dephosphorylation of a target peptide.
Figure 16B:
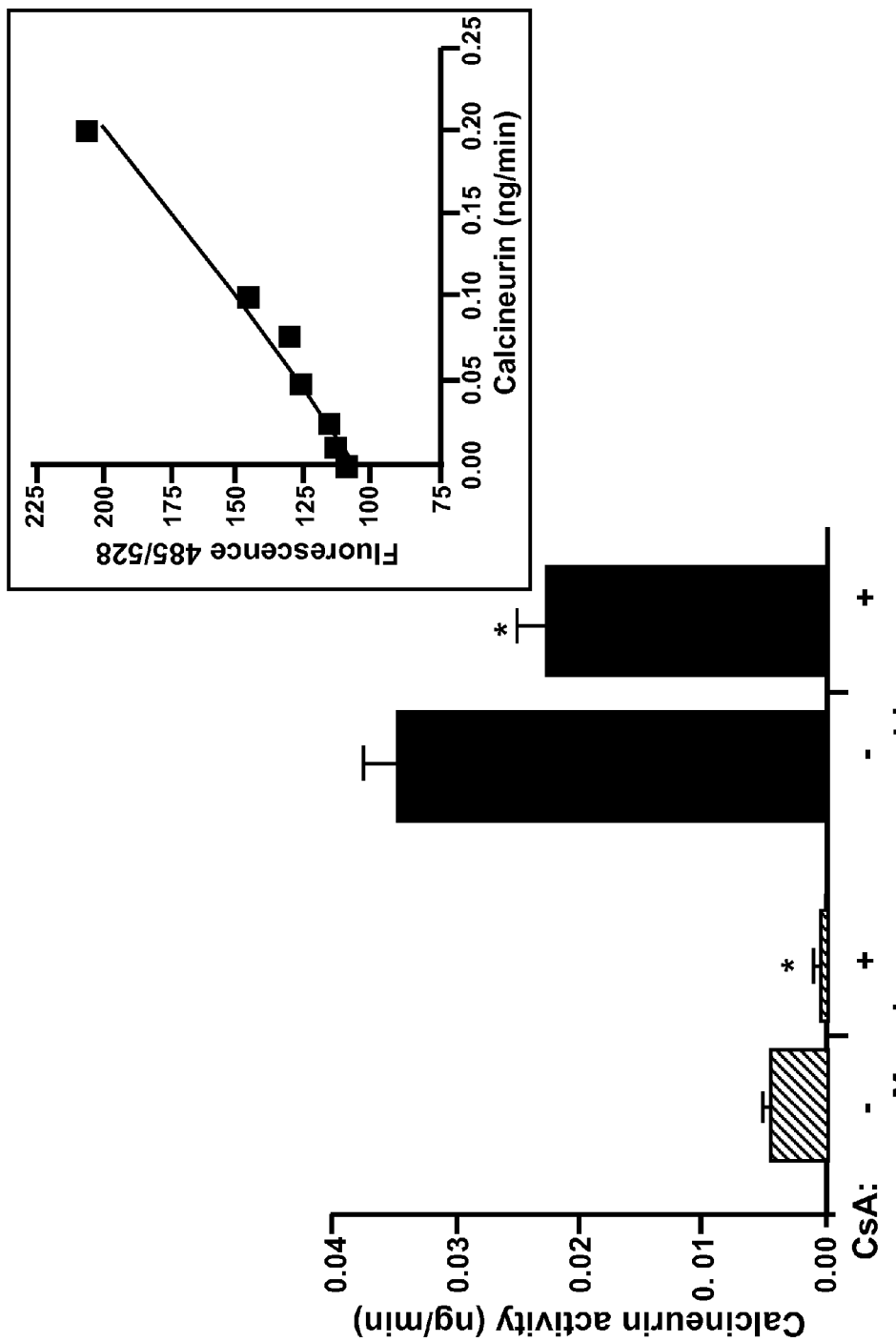

The use of the new calcineurin assay in two systems was explored. FIG. 16A shows the result of calcineurin stimulation by a variety of agents in cultured primary renal fibroblasts. When the absorbance values obtained were compared to a standard curve of recombinant calcineurin run simultaneously, a determination of calcineurin activity in each condition can be made. Arginine vasopressin (AVP), dexamethasone, and phorbol myristate acetate (PMA) each significantly stimulated calcineurin activity. Pre-treatment with the calcineurin inhibitor FK506 (tacrolimus) blocked stimulation by PMA. Next, protein lysates were collected from liver and muscle samples of mice treated with vehicle alone or treated daily with 20 mg/kg cyclosporine A. Calcineurin assays were performed on 1 μg of total protein. Results indicated that there is significantly more calcineurin activity per μg protein in the liver compared to muscle. Cyclosporine treatment significantly decreased calcineurin activity in both tissues (FIG. 16B).

Acidic peptides (other than phosphopeptides) also show affinity for titanium oxide. The RII peptide is, in fact, rather acidic even when not including phospho-Ser-15 (5 negative and 3 positive charges); however this does not negatively influence the ruggedness and reproducibility of the assay. $^{32}$P-based assays are very specific as they measure inorganic phosphate released upon the action of the phosphatase. The embodiments of the assay method of the present disclosure, on the other hand, measure fluorescence of the probe attached to unbound peptide released to solution due to the loss of phosphate (which causes loss of binding affinity to titanium oxide). However, it is possible that the fluorescence probe may also be released in solution by the action of a protease, e.g. a tryptic-like enzyme present in the biological material, cleaving the substrate at the C-terminal side of arginines. In such case, peptide fragments such as Fluoresceinyl-DLD-VPIPGR will be released simulating phosphatase activity, and thereby presenting false positive results. Hence, inclusion of protease inhibitors is preferred to minimize such artifacts.

The fluorimetric method of the present disclosure is not limited to the incorporation of a fluorescein tag, and it is contemplated that the peptides of the assay may be modified with other fluorescent moieties. Fluorescein can be quenched by common reagents including dithiothreitol and its excitation can be altered with pH and light exposure. Use of fluoresceine requires the reaction to be protected from light and neutralized prior to fluorimetry. Other tags suitable for incorporation into the peptide substrates for use in the methods of the present disclosure include, but are not limited to such as TAMRA, which may be less pH- and light-sensitive.

To further evaluate the reproducibility of the method, 14 separate samples with 6 replicate reactions were analyzed. The intra-assay variability was 9.35%, a better variability rate than achieved with previous methodologies.

The present disclosure further encompasses assays that comprise the peptide substrate that can be selectively dephosphorylated by the β isoform of calcineurin and not the α isoform. The amino acid sequence of the isoform-specific peptide substrate is based on a portion of the NFATc protein, a known substrate of calcineurin, which has been modified to improve isoform selectivity and ease of synthesis. The amino acid sequence of the peptide is ASPQTSPWQSPAVSPK (SEQ ID NO.: 2) wherein the Ser-6 position may be phosphorylated. A fluorescently labeled version of the peptide is as follows: ASPQT(pS)PWQSPAVSPK with an N-terminal fluorescent TAMRA group and a C-terminal amide group, although it is contemplated that a fluorescent group other than TAMRA may be substituted without affecting the efficacy of the substrate.

(c) FRET-Based Fluorimetric Calcineurin Assay

Figure 17:
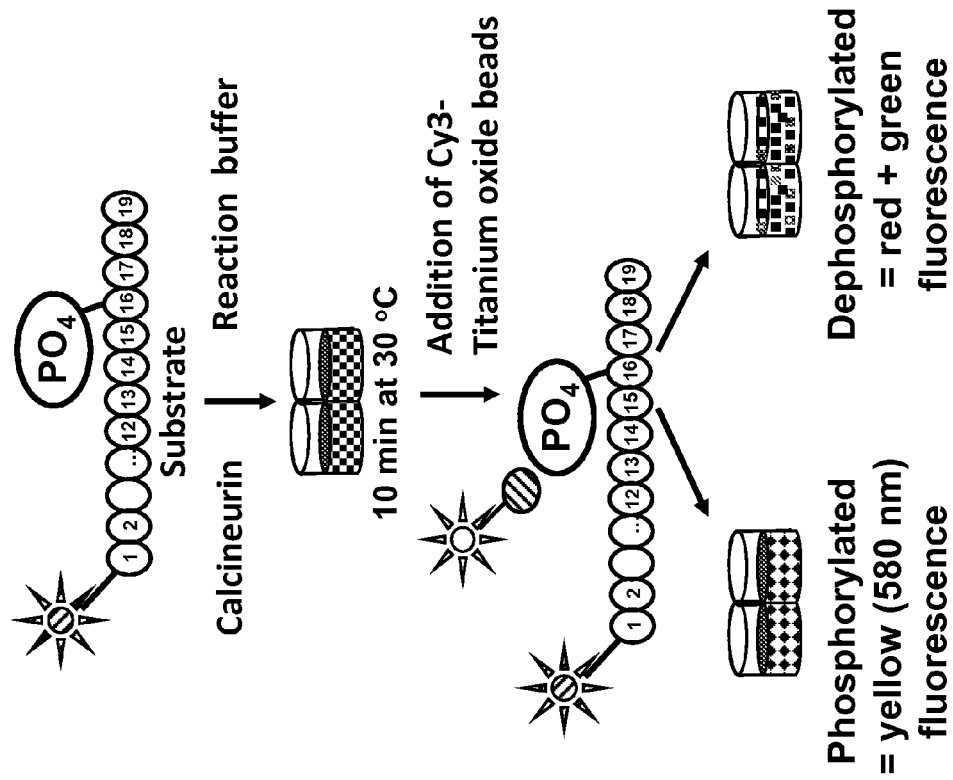
FIG. 17 schematically illustrates a FRET-based assay of calcineurin activity.
Figure 18:
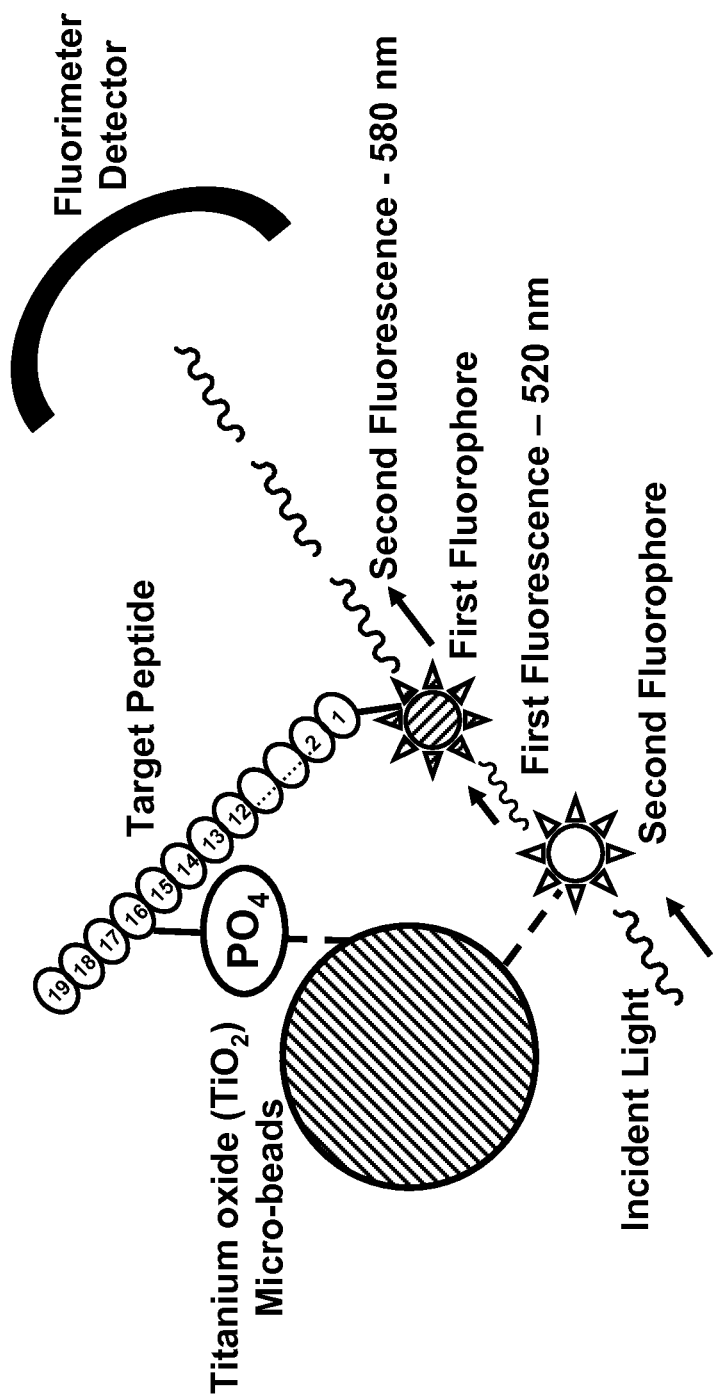
FIG. 18 schematically illustrates the FRET formation of a detectable fluorescence due to binding of a phosphorylated peptide on titanium oxide micro-beads.
Figure 19:
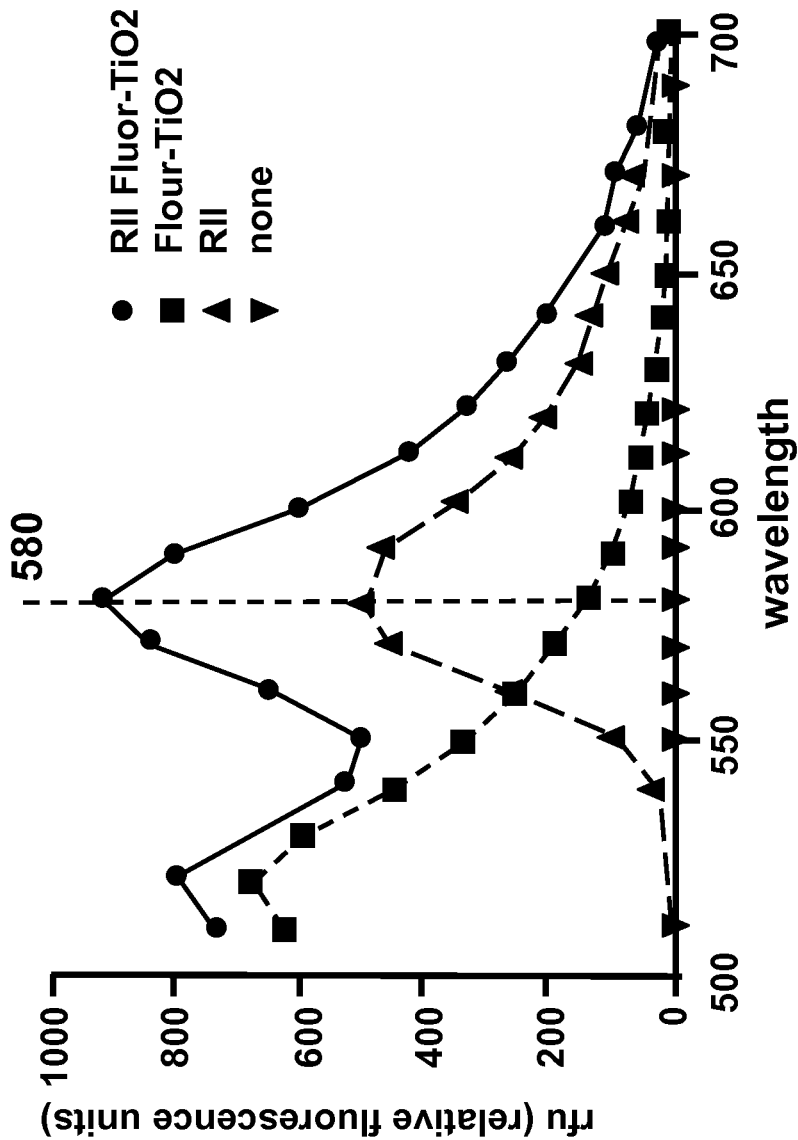
FIG. 19 is a graph illustrating the FRET between FLOUR-titanium oxide and TAMRA-peptide RII. FLOUR-beads alone emit a peak at approximately 520 nm; TAMRA-peptide alone emits a detectable background peak at 580 nm and the combination of the two produces a shift of the 580 nm peak.
Figure 20A:
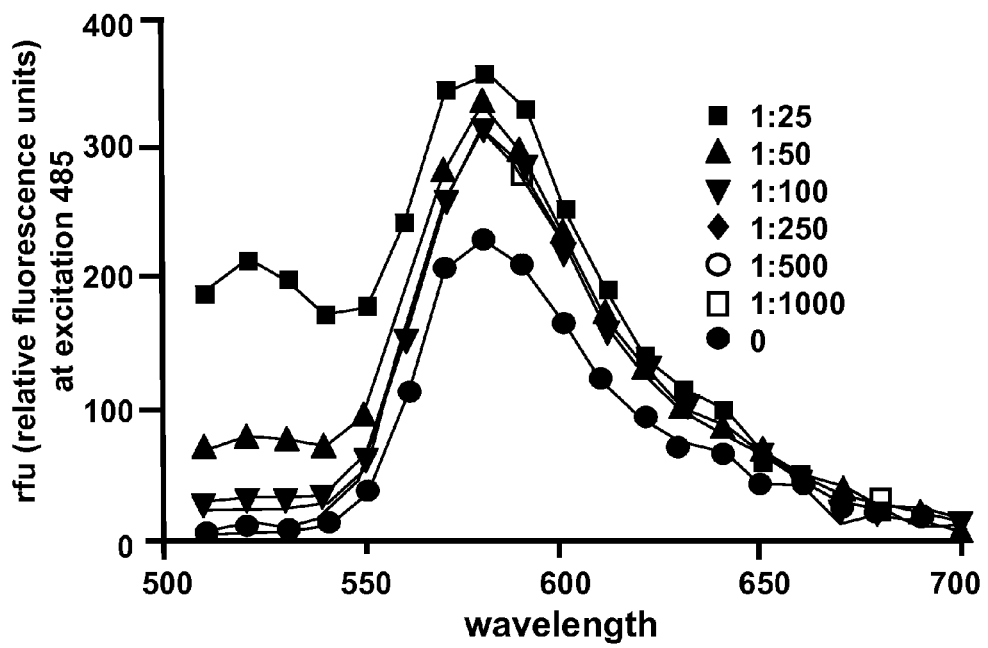
FIGS. 20A and 20B show a pair of graphs illustrating response of the FRET 580 nm peak as a function of FLUOR-bead concentration (FIG. 20A) or TAMRA-RII peptide concentration (FIG. 20B).
Figure 20B:
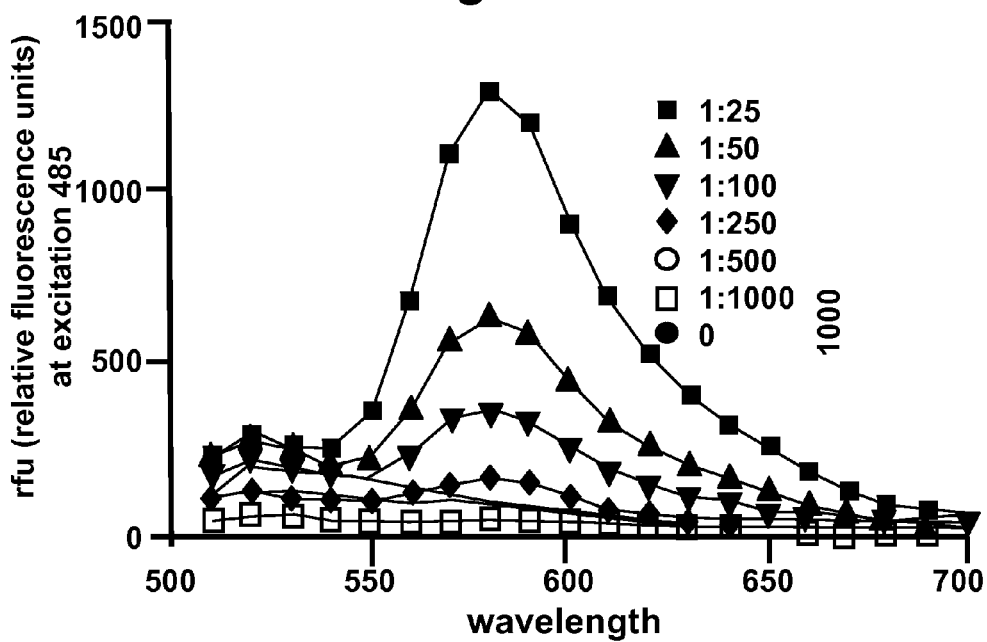
Figure 21A:
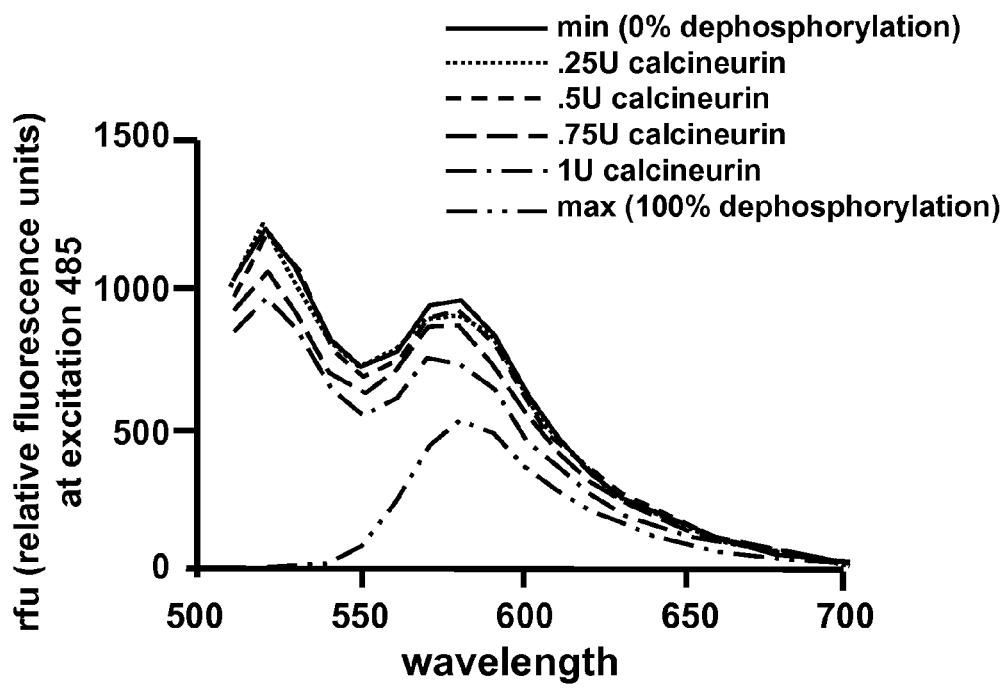
FIG. 21A is a graph illustrating the FRET response to increasing amounts of calcineurin. The 580 nm peak was compared with the reactions containing only TAMRA-peptide RII and no beads (designated max or 100% dephosphorylation) and with a reaction containing TAMRA-peptide RII and beads, but no calcineurin (designated minimum or 0% dephosphorylation).
Figure 21B:
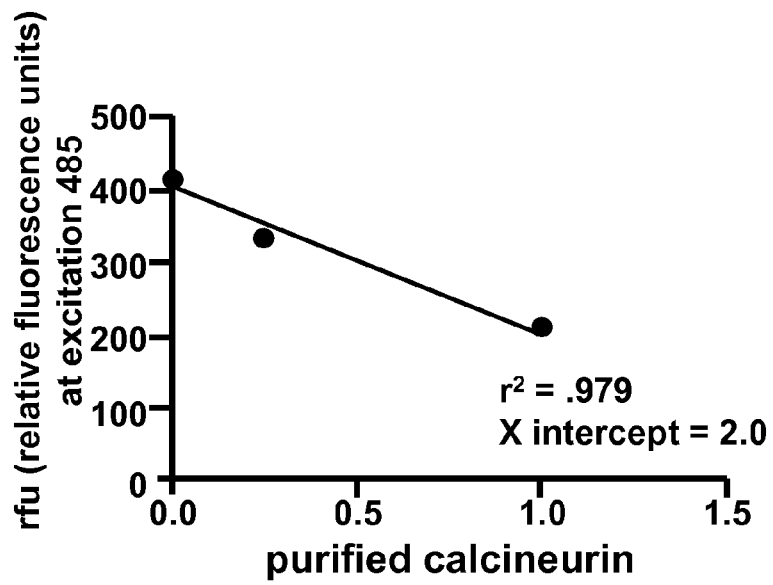
FIG. 21B is a graph illustrating the linear dose effect of calcineurin concentration. The curve could be used to extrapolate calcineurin activity from a range of 0 units to about 2 units under the experimental conditions.

In the FRET-based methods of the present disclosure, schematically presented in FIGS. 17 and 18, the titanium oxide partitioning agent is provided as micro-beads conjugated to a second fluorescent moiety such as fluorescein. The second fluorophore conjugated to the titanium oxide micro-beads is selected whereby, when excited by an incident light, will emit a light at a wavelength that corresponds to the activation wavelength of the first fluorophore conjugated to the target peptide. Therefore, for example, upon illumination of the assay mixture with light of a suitable excitation wavelength, the green signal from the fluorescein transfers energy to the TAMRA tag of a target labeled peptide, which then provides a unique emission, as shown in FIG. 19.

The assay according to the present disclosure only detects the secondary fluorescence emitted by FRET, and not of unbound peptide. The light detection apparatus used to detect the fluorescence light may be adapted by the use of such as wavelength-specific filters, to selectively detect one wavelength and not another. Additionally, the reaction using titanium oxide as the method of partitioning modified from unmodified target peptide may be conducted in a single reaction mix and reaction step. The methods of the present disclosure do not require the multi-step procedure of reacting assay components and partitioning bound from unbound peptide before directly determining the amount of the fluorescently labeled peptide not bound to titanium oxide. The method of the present disclosure, therefore, is particularly suitable, and may be readily adapted, for automation.

Accordingly, the micro-beads may be separated from the assay mix supernatant by such as filtration, centrifugation, or by having previously bound the micro-beads to a solid substrate. In the latter case, the reaction mixes maybe contacted to the substrate-bound micro-beads, and after a suitable reaction period the reaction mix may be replaced by a wash solution before determining the FRET fluorescence. The peak of emission from the first fluorophore can then be detected and used to quantitatively determine the amount of phosphorylated substrate in each reaction. Results of experimental samples are compared to a standard curve generated phosphatase and units of activity calculated. Characterizations of the FRET-based assay as used in the methods of the present disclosure are presented in FIGS. 20A-21B.

One aspect of the present disclosure, therefore, encompasses methods for determining the response of a human or animal subject to an immunosuppressive therapeutic agent, embodiments of the methods comprising: (i) obtaining an isolated population of T cells from a human or animal subject in receipt of an immunosuppressive therapeutic agent; (iii) lysing the isolated population of T cells; (ii) dividing the lysed isolated T cell population into at least a first aliquot and a second aliquot; (iv) determining a first level of calcineurin activity in the first aliquot of lysed T cells; (v) contacting the second aliquot of lysed T cells with a composition comprising a T cell receptor agonist and then determining a second level of calcineurin activity in the second aliquot of lysed T cells; and (vi) comparing the first and the second levels of calcineurin activity as determined in steps (iv) and (v) respectively, whereby the ratio of the first and the second levels of calcineurin activity indicates the degree of responsiveness by the human or animal subject to the immunosuppressive therapeutic agent.

In embodiments of this aspect of the disclosure, the prediction of the response of a human or animal subject to an administered immunosuppressive therapeutic agent may provide a prognosis of a transplant in the human or animal subject.

In embodiments of the methods of this aspect of the disclosure, the T cell agonist can be an anti-CD3-specific antibody.

In some embodiments of this aspect of the disclosure, the composition comprising a T cell receptor agonist may further comprise a T cell co-stimulator. In these embodiments, the T cell co-stimulator can be an anti-CD28-specific antibody.

In the embodiments of this aspect of the disclosure, the first and the second levels of calcineurin activity may be determined by a radiometric assay or by a fluorimetric assay.

In some embodiments of the methods of this aspect of the disclosure, the fluorimetric assay can be a FRET-based fluorimetric assay.

In an embodiment of the disclosure, the composition comprising a T cell receptor agonist does not comprise a T cell co-stimulator, and the first and the second levels of calcineurin activity can be determined by a FRET-based fluorimetric assay.

In embodiments of the disclosure, the human or animal subject is a transplant recipient. In some embodiments of this aspect of the disclosure, the fluorimetric assay may comprise the steps of: (a) contacting in a reaction mix the first aliquot of lysed T cells and a fluorescently labeled phosphorylated target peptide substrate capable of being dephosphorylated by calcineurin, wherein the target peptide comprises an amino acid sequence selected from SEQ ID NO.: 1 and SEQ ID NO.: 2, under conditions allowing calcineurin to dephosphorylate the target peptide; (b) contacting the reaction mix with a titanium oxide matrix, thereby partitioning phosphorylated target peptide from dephosphorylated target peptide; and (c) determining the intensity of the fluorescence of the fluorescently labeled dephosphorylated target peptide, thereby detecting calcineurin activity; and (d) correlating the intensity of the fluorescence to the calcineurin activity, said correlating step comprising: (i) providing a test sample, wherein the test sample comprises a known amount of calcineurin activity, and repeating steps (a)-(f) on said test sample, thereby obtaining a value of the second fluorescence intensity corresponding to the known amount of the calcineurin; and (ii) comparing a value of the second fluorescence intensity generated from an aliquot of lysed T cells with the value of the second fluorescence intensity obtained with the known amount of calcineurin, thereby determining the amount of calcineurin activity in the aliquot of isolated T cells. In these embodiments, step (b) may comprise: (i) obtaining a reaction vessel, wherein the reaction vessel is coated with a titanium oxide matrix, and wherein the titanium oxide matrix is contacted with a binding buffer; (ii) delivering the reaction mix to the coated vessel, and incubating under conditions allowing binding of fluorescently labeled phosphorylated peptide to the titanium oxide matrix; (iii) transferring the reaction mix from the coated well to a vessel containing ammonium hydroxide; and (iv) determining the amount of fluorescence emitted by fluorescently labeled dephosphorylated peptide in the reaction mix.

In embodiments of this aspect of the disclosure, the assay method can be configured for high-throughput screening of a plurality of test samples. In these embodiments, the assay method is configured for automated high-throughput screening of a plurality of test samples.

In some of the embodiments of this aspect of the disclosure, the target peptide may have the amino acid sequence according to SEQ ID NO.: 1, is phosphorylated on the Ser-15 position.

In one embodiment, the target peptide is capable of being specifically dephosphorylated by the β-isoform of calcineurin and comprises the amino acid sequence according to SEQ ID NO.: 2, wherein the S-6 position is phosphorylated.

In other embodiments of this aspect of the disclosure, the FRET-based fluorimetric assay can comprise: (a) providing an assay reaction mix comprising a target peptide comprising an amino acid sequence specifically recognized by calcineurin, wherein the target peptide comprises an amino acid sequence selected from SEQ ID NO.: 1 and SEQ ID NO.: 2, a phosphate group conjugated to said target peptide, and a first fluorophore species conjugated to said target peptide; a buffer mix configured to allow calcineurin to dephosphorylate the target peptide; and a test sample comprising an aliquot of lysed T cells; (b) incubating the assay reaction mix under conditions suitable for calcineurin to dephosphorylate the target peptide; (c) contacting the incubated reaction mix with titanium oxide, said titanium oxide having a second fluorophore species conjugated thereon, under conditions suitable for the titanium oxide to bind to a phosphorylated target peptide but not to a dephosphorylated target peptide; (d) illuminating the titanium oxide at an excitation wavelength of the second fluorophore species, whereby the second fluorophore species emits a first fluorescence, said first fluorescence exciting the first fluorophore species by FRET, thereby inducing the emission of a second fluorescence from the first fluorophore species, said second fluorescence having a wavelength different from the wavelength of the first fluorescence; (e) selectively detecting the second fluorescence, thereby detecting binding of phosphorylated target peptide to titanium oxide; (f) determining the intensity of the second fluorescence; and (g) correlating the intensity of the second fluorescence to an amount of calcineurin activity, said correlating step comprising: (i) providing a test sample comprising a known amount of calcineurin activity, and repeating steps (a)-(f) on said test sample, thereby obtaining a value of the second fluorescence intensity corresponding to the known amount of the calcineurin; (ii) comparing a value of a second fluorescence intensity generated from an aliquot of lysed T cells with the value of the second fluorescence intensity obtained with the known amount of calcineurin, thereby determining the amount of calcineurin activity in the aliquot of isolated T cells.

In embodiments of the FRET-based assay system, the titanium oxide is formulated as micro-beads, and wherein the micro-beads are suspended in the assay reaction mix. In these embodiments, the assay method may be configured for automated high-throughput screening of a plurality of test samples.

In some embodiments, the target peptide can have the amino acid sequence according to SEQ ID NO.: 1, and is phosphorylated on the Ser-15 position.

In other embodiments, the target peptide can be capable of being specifically dephosphorylated by the β-isoform of calcineurin and comprises the amino acid sequence according to SEQ ID NO.: 2, where the S-6 position is phosphorylated.

Another aspect of the disclosure encompasses kits for determining the level of calcineurin activity in a test sample, comprising a container enclosing a fluorescently labeled target peptide selectively recognizable by a calcineurin; a T cell receptor stimulator, and instructions for the use of the target peptide in determining the calcineurin activity of a test sample comprising an aliquot of lysed isolated T cells, whereby a level of calcineurin activity or a ratio of said levels indicates the degree of responsiveness by the human or animal subject to the immunosuppressive therapeutic agent.

In these embodiments of this aspect of the disclosure, the prediction of the response of a human or animal subject to an administered immunosuppressive therapeutic agent can further provide a prognosis of a transplant in the human or animal subject.

In other embodiments of this aspect of the disclosure, the kits may further comprise a titanium dioxide matrix or an amount of titanium oxide micro-beads, where the micro beads have a fluorophore conjugated thereto.

In embodiments of this aspect of the disclosure, the target peptide has an amino acid sequence selected from the group consisting of SEQ ID NOs.: 1 and 2.

In other embodiments of the kits of this aspect of the disclosure, the kits may further comprise at least one of the group consisting of a reaction buffer, a cell lysis buffer, a binding buffer, a reaction mix for phosphorylating the target peptide; an ammonium hydroxide solution; and at least one calcineurin activity standard solution.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Materials and Reagents

Recombinant calcineurin was from Calbiochem (San Diego, Calif.), and all other chemicals were obtained from Sigma (St Louis, Mo.). The RII peptide, Fluoresceinyl-DLD-VPIPGRFDRRVSVAfrican-AmericanE, and its phosphorylated analog (Fluoresceinyl-DLDVPIPGRFDRRVpSVAfrican-AmericanE where pS=L-phosphoserine) were synthesized by Fmoc-based solid-phase peptide synthesis using model Liberty microwave-assisted peptide synthesizer (CEM Corporation, Matthews, N.C.). The peptides were purified to apparent homogeneity by reversed-phase HPLC and their masses were confirmed by mass spectrometry. Peptides were diluted in: Tris 50 mM, 100 mM NaCl, 0.5 mM DTT, and 0.1 mg/ml bovine serum albumen to a final concentration of 30 ng/ml. Reaction buffer consisted of 0.1 mg/ml BSA, 35 mM Tris pH 7.5, 25 mM NaCl, 2.0 mM $MgCl_2$, 270 μM DTT, 500 μM EDTA, 419 nM Okadaic acid (in 0.63% ethanol), 25 mM $CaCl_2$. Titanium oxide plates were pre-incubated with a binding buffer consisting of 0.1% acetic acid in 10% acetonitrile.

Example 2

T Cell Isolation and Treatment 40 mLs of heparinized blood was collected from the study participants. T cells were then isolated using the Prepacyte SC reagent (BioE WBP2000 St. Paul Minn.) antibody negative selection and Vitalyse (BioE KI-135) treated to eliminate remaining erythrocytes. Cells were pelleted by centrifugation, washed with 1× phosphate-buffered saline, and resuspended in RPMI 1640 containing penicillin/streptomycin antibiotics, 10% fetal calf serum, 2 mM 1-glutamine, 25 mM glucose, and 1 mM sodium pyruvate. Resulting cells were identified by flow cytometry and found to be 98-99% CD3+, CD4+. For treatment with inhibitors, isolated T cells were separated into equal aliquots and preincubated for 15 minutes with FK506 (5 ng/ml), cyclosporine A (5 μg/ml) or DMSO then, if stimulated, treated for 30 minutes with anti-CD3/anti-CD28 antibodies (10 μg/ml each) (BD Biosciences, San Jose, Calif.).

Example 3

Radiometric Calcineurin Assay

Calcineurin activity was determined using an in vitro assay as described in Fruman et al, *Methods in Enzymology* 9, 146-154 (1996) and Lea et al., *J Am Soc Nephrol* 13, 1750-1756 (2002), both of which are incorporated herein by reference in their entireties. Following treatment, isolated lymphocytes were pelleted and then re-suspended in calcineurin buffer (104 μM Tris, 250 μM KCl, 10 mg/ml BSA, 5 mg/ml DTT, pH 7.5). Cells were then lysed by three cycles of freeze-thawing in liquid nitrogen and a 37° C. water bath. The concentration of harvested proteins was determined by the BCA method (Pierce Biotechnology, Rockford, Ill.) and then 10 μf of sample was incubated with equal volumes of calcineurin reaction buffer (100 nM calmodulin, 0.1 mM CaCl, 25 µgs calyculin, 3 µg cold RII peptide) and 30 $\gamma^{32}$P[ATP]-labeled RII peptide substrate.

The reaction was allowed to proceed for 10 minutes, and then 10 mgs/ml charcoal/TCA solution was added to each sample to stop the reaction. Finally, samples were passed through millipore filtration buckets, scintillation fluid added, and the amount of released phosphates read in an automated counter. Reactions were performed in triplicate and final data for subjects were calculated as the mean of triplicate samples minus control reactions to normalize for background.

Example 4

Fluorimetric Calcineurin Assay (i) Collection of samples. Heparinized blood can be obtained by routine phlebotomy and PBMC isolated and frozen in 10% DMSO. Samples will be thawed and viability confirmed prior to treatment.

(ii) Treatment of T cells. Three parameters of calcineurin activity: 1) base-line levels of the enzyme; 2) the increase in calcineurin in response to general stimuli; and, 3) the response of calcineurin to T cell receptor specific activation. PBMCs were thawed, viable cells counted and then separated into aliquots of about $2 \times 10^5$ cells. Based on preliminary experiments, samples were treated with anti-CD3 (Muromonab, 10 µg/ml) antibodies for 15 mins at 37° C. Based on preliminary dose and time curves, PMA was added to aliquots for 5 mins. Control samples were included with either no treatment or adjuvant-only (DMSO). These manipulations yielded base-line activity, maximum non-specific activation, and TCR-stimulated activity.

(iii) 20 µl diluted peptide substrate, 20 µl of reaction buffer, and 20 µl of sample were loaded into individual wells of a 96-well plate and incubated at 30° C. for 10 minutes. During the reaction time, a 96-well plate with titanium oxide-coated wells was prepared by adding 50 µl binding buffer (0.1% acetic acid in 10% acetonitrile) per well. After the incubation period, reactions were transferred into prepared titanium oxide-coated wells following by gentle shaking for 5 minutes. The contents of each well were then removed to a white 96-well plate preloaded with 20 µl of 3N ammonium hydroxide. The amount of fluorescent label that did not bind to the titanium oxide matrix was quantified by fluorimetry at 485 nm excitation 528 nm emission.

Example 5

FRET Fluorimetric Calcineurin Assay

Briefly, a peptide substrate was synthesized that incorporated a phosphoserine residue and an N-terminal TAMRA fluorescent tag. Protein lysates are incubated with the peptide in a reaction buffer and active calcineurin removes the phospho group from the serine residue. Phosphorylated peptide and non-phospho peptides are separated by incubating reactions with titanium-oxide beads labeled with the fluorophore fluorescein (FLOUR). Phosphorylated peptide bind to the beads while non-phosphorylated peptides will remain unbound. The combination of FLOUR and TAMRA then produces a shifted peak that can be quantitated. The amount of active calcineurin can then be determined by comparing the shifted fluorescence to a standard curve of recombinant calcineurin.

(i) Peripheral mononuclear blood cells (PMBCs) were pelleted, resuspended in a hypotonic lysis buffer (see Gooch et al., *J. Biol. Chem.* 276 (2001) 42492-500; Gooch et al., (2004) *J. Biol. Chem.* 279: 15561-70; incorporated herein by reference in their entireties) and then lysed by three rounds of freeze/thawing in liquid nitrogen and a 30° C. water bath. This ensured that the cell membranes were ruptured in an isotonic buffer that did not interfere with calcineurin activity.

Calcineurin activity was assessed by mixing equal parts lysate, RII or other peptide substrate (20 µl diluted peptide substrate, 20 µl of reaction buffer, and 20 µl of test sample), and reacted for 5-10 mins at 30° C. Control reactions were included that contained known varying amounts of purified calcineurin to calculate a standard curve for each plate.

(iii) To stop the reaction, a solution of 10% acetyl nitrile and 0.01% acetic acid solution was added. This step was essential to reduce the pH of the reaction to below 3.5 and enable the binding of the titanium oxide beads to the target peptide.

(iv) FLOUR-titanium oxide beads were added with gentle shaking for 5 mins. Phosphorylated-peptides were retained on the beads producing a "shifted" TAMRA signal while non-phosphorylated peptides were unbound.

(v) Reactions were neutralized with 0.35% ammonium hydroxide to return the pH to greater than 7 and the fluorescence of each sample will be read at 450 nm excitation/580 nm emission.

(vi) Calcineurin activity was then determined by calculating the slope and y-intercept of the standard curve and then extrapolating calcineurin activity from the fluorescence intensity. Triplicate reactions will be averaged to arrive at a final measurement for each sample stated as U of Calcineurin activity/$1 \times 10^6$ cells/minute.

Hypotonic Lysis Buffer: 50 mM Tris pH 7.5, 1 mM EDTA, 1 mM EGTA, 0.5 mM DTT, 50 µg/ml PMSF, 10 µg/ml leupeptin, 10 µg/ml aprotinin.

Reaction Buffer: 0.1 mg/ml BSA, 35 mM Tris pH 7.5, 25 mM NaCl, 2.0 mM $MgCl_2$, 270 µM DTT, 500 µM EDTA, 419 nM Okadaic acid (in 0.63% ethanol), 25 mM $CaCl_2$.

Example 6

Cytokine Array

Cytokine arrays were carried out according to the manufacturer's instructions (Panomics Cytokine Array, Fremont Calif.). Briefly, array membranes were incubated for 1 hour in 1× blocking buffer, and then incubated with the biotin-conjugated anti-cytokine mix for 2 hours. The membranes were then incubated with streptavidin/horseradish peroxidase-conjugated secondary antibody at room temperature for 30 minutes. Finally, following treatment with detection buffer for 5 minutes, membranes were developed with ECL, visualized by radiography, and quantitated by densitometry. Each duplicate spot of cytokine was normalized to internal controls provided by the manufacturer. Data was obtained as the fold difference in each cytokine compared to the internal controls.

Example 7

Statistics: All statistical calculations were carried our using GraphPad Prism scientific graphing and analysis software. Paired T tests and repeated measure analysis of variance (ANOVA) were used as indicated to compare multiple treatments of individual samples. For comparison of 3 or more groups, ANOVA (or repeated measure ANOVA, as appropriate) was used in conjunction with Tukey's post-test. Comparison of two sets of variables was completed by two-way ANOVA as indicated. All results were considered significant if p<0.05.

Example 8

To compare calcineurin activity in circulating T cells, blood was obtained from 81 normal controls and 39 patients with functioning renal allografts. Patients undergoing bone marrow transplantation or other forms of solid organ transplantation were excluded. All normal controls were reported as healthy and free of hypertension, diabetes or chronic renal disease. The demographics of renal transplant patients and normal controls including age, height, weight, gender and racial identification are shown in Table 2. Both control and transplanted cohorts were approximately 50% male and 50% female.

TABLE 2

Demographic characteristics of study participants

| Groups | N | Gender Male-female | Race CC[a]----AA[b]---Asian | Age | BMI |
|---|---|---|---|---|---|
| Control | 81 | 49.0%-51.0% | 49.4%--45.7%--4.9% | 34.5 | 27.4 |
| Control (subset) | 30 | 50.0%-50.0% | 50.8%--41.0%--8.2% | 34.5 | 27.5 |
| Transplant | 39 | 56.4%-43.6% | 48.7%--46.2%--5.1% | 47.5 | 28.6 |

[a]CC: Caucasian
[b]AA: African-American

The average age of controls was 35.3, and the average body mass index was 27.5. The average age and BMI of the post-transplant patients were higher than the control group at 47.5 years and 28.6, respectively. Both groups were racially diverse with about half Caucasians and half African Americans.

The duration of renal transplantation ranged from 1 month to 14 years (mean 22 months). 20 patients (51%) were transplanted within one year of study enrollment, while the remaining 19 (49%) patients were greater than one year post-transplant. All transplant patients were currently taking calcineurin inhibitors with 31 taking tacrolimus and 8 receiving Cyclosporine A. Plasma levels of tacrolimus and Cyclosporine A were within therapeutic ranges and averaged 11.4 and 172 ng/ml, respectively.

Example 9

Calcineurin Activity in the Control Cohort

To ensure that calcineurin activity was measured in a uniform population of cells, experiments were performed in isolated lymphocytes that were enriched for $CD3^+/4^+$ T cells using erythrocyte lysis, gradient centrifugation, and Prepacyte SC reagent (BioE, St. Paul Minn.). Flow cytometric analyses confirmed that over 98% of isolated lymphocytes were $CD3^+/4^+$ T cells.

First, T cells were isolated from control subjects and were then treated in vitro with vehicle (DMSO) or 5 ng/ml tacrolimus for 15 minutes. FIG. 2 shows that tacrolimus significantly reduced calcineurin activity from 913±6 fmole/µg protein/min to 662±6 fmole/µg protein/min (p<0.001). Females in the control cohort had statistically lower levels of activity compared to males (1073±133 fmole/µg protein/min versus 758±75 fmole/µg protein/min (p<0.05). Despite differences in basal activity, both male and female subjects exhibited equal sensitivity to tacrolimus (27±4% inhibition versus 30±4% respectively) (FIG. 3).

Example 10

The effect of stimulating the T cell receptor (TCR) with anti-CD3/anti-CD28 antibodies on calcineurin activity was examined. As shown in FIG. 3, calcineurin activity increased significantly from 1214±111 fmole/µg protein/min to 1652±138 fmole/µg protein/min (p<0.001) in the control (non-transplanted) group. Pre-treatment of the isolated cells with either tacrolimus or cyclosporine A (5 µg/ml) blocked the rise in calcineurin activity. There were no gender differences in the activation of calcineurin or the inhibitory effect of tacrolimus or cyclosporine A. There was no significant correlation between calcineurin activity and age, body mass index (BMI), or race in the control cohort.

TABLE 3

Calcineurin activity and patient demographics

| | Control | | Transplant | |
|---|---|---|---|---|
| | Basal | TCR-stimulation | Basal | TCR-stimulation |
| Age | .037/ns | .108/ns | −.2 | −.025/ns |
| BMI | −.220/ns | .067/ns | | .078/ns |
| Race | .292/ns | .128/ns | .314/ns | .212/ns |
| tacrolimus (trough) | n/a | n/a | .091/ns | −.208/ns |

Basal and TCR-stimulated calcineurin activity and study participant characteristics were analyzed by Pearson Correlation. Data shown are the Pearson r/p value (if less than 0.05).

Example 11

Calcineurin Activity in Post-Transplant Subjects

Calcineurin activity was measured in T cells isolated from 39 post-renal transplant subjects. Compared to normal controls, calcineurin activity was significantly higher than in renal transplant patients (1776±175 fmole/µg protein/min versus. 914±78 fmole/µg protein/min) (p<0.001), as shown in FIG. 4. In contrast to control subjects (shown in FIG. 2), calcineurin activity in male transplant recipients was lower compared to females (p<0.01). As a result, a significant increase was observed when female control and transplant patients were compared, while the difference between male control and transplant subjects did not reach significance.

Example 12

Isolated T cells from the transplant cohort were stimulated with anti-CD3/anti-CD28 antibodies. In contrast to TCR stimulation in controls (shown in FIGS. 3, 5A, and 5B), anti-CD3/anti-CD28 antibody-treatment did not increase calcineurin activity in the transplant cohort (FIG. 5C). Moreover, the mean increase in calcineurin activity for the control group was significantly higher at 36% (FIG. 5A) compared to only 3% for the transplant group (FIG. 5B).

Increased basal calcineurin, but with decreased TCR-stimulated calcineurin activity in transplant subjects suggests that basal and stimulated calcineurin activities are inversely related. To examine this, basal and stimulated calcineurin were compared by linear regression.

FIGS. 6A and 6B show that there is a significant inverse association between basal and TCR-stimulated calcineurin in both the control (FIG. 6A) and transplant cohorts (FIG. 6B). Baseline calcineurin activity progressively rose following transplantation, and TCR stimulation decreased, as shown in FIG. 7.

Basal calcineurin activity at one month was 1491±316 fmole/µg protein/min, rising to 2117±150 fmole/µg protein/min at one year, and 3834±987 fmole/µg protein/min by year three. TCR stimulation decreased over the same period. There was no difference in trough tacrolimus levels between any of the groups.

Example 13

Mass Spectrometry

The system used for the analysis was an Ultimate capillary HPLC system (LC Packings) with a FAMOS autosampler. An 0.5×150 mm C18SB-300 Zorbax (Agilent, Technologies, Palo Alto, Calif.) reversed-phase column was used as the analytical column. The LC eluent was directly sprayed into the 4000QTRAP mass spectrometer using a TurboV electrospray ion source (Applied Biosystems, Foster City, Calif.). Elution from the column was accomplished with an acetonitrile gradient from 2% to 80% with 0.1% formic acid as a counter ion for HPLC. The flow rate was set at 15 µl/min. The total LC run time was 60 minutes including equilibration. The 4000Qtrap was operated both in the information dependent acquisition (IDA) mode and straight MS mode. In IDA, for each cycle, a single MS spectrum was acquired followed by up to two MS/MS spectra based upon observed ions in the MS spectrum. The MS spectrum was acquired over the m/z range of 350 to 1,350. Each MS/MS spectrum was acquired over the m/z range of 50 to 1,350. Precursors were determined by each cycle's MS spectrum from the m/z range of 375 to 1,100. Straight MS was performed over the m/z range of 350 to 1,350. For each sample, extracted ion chromatograms (XIC) were generated for the phosphorylated and non-phosphorylated versions of the RII peptide. The width used for the XIC was 1 Dalton. Based on the areas of the peaks from each XIC, the relative quantity of phosphorylated to non-phosphorylated peptide was determined.

Example 14

Calcineurin is the target of immunosuppressive drugs but very little is known about how calcineurin activity changes in T cells of transplant patients. To begin, a random group of control subjects (see Methods) was recruited. Gender, age, height, weight, and racial identification were self-reported by the volunteers. 50% were male, 50% female, the average age was 35.3, and the average body mass index was 27.5.5% were Asian, 45% Caucasian, and 50% African American (see Table 2). Blood was drawn from 82 subjects and T cells were isolated by negative antibody selection using Prepacyte SC reagent. Calcineurin activity was determined using an in vitro assay as previously described by Fruman et al., *Methods in Enzymology* 9, 146-154 (1996), and Gooch et al., *J. Biol. Chem.* 279, 15561-70 (2004), incorporated herein by reference in their entireties.

T cell isolates were stimulated for 15 minutes with multiple agents including calcium ionophore, phorbal myristate acid (PMA), and anti-CD3/CD28 antibodies. CD3/CD28 co-stimulation resulted in the most consistent and robust stimulation of calcineurin activity. When compared with basal, unstimulated levels, CD3/CD28 co-stimulation resulted in a significant increase in calcineurin activity (paired T-test), as shown in FIG. 22A. Next, T cells were pre-treated for 30 minutes with cyclosporine (5 mg/ml) or FK506 (5 ng/ml) and then CD3/CD28-mediated stimulation was measured. Both cyclosporine A and FK506 significantly reduced CD3/CD28-mediated calcineurin activity (ANOVA, Tukey's posts-test), as shown in FIG. 22B.

Thirty-nine patients who were receiving outpatient care and who had undergone kidney transplant were recruited for the study. Demographic data (Table 1) was obtained as well as post-transplant characteristics, as shown in Table 5.

TABLE 4

Study group characteristics

| Groups | N | Gender | | Race | | | | Age | BMI |
| --- | --- | --- | --- | --- | --- | --- | --- | --- | --- |
| | | Male | female | Caucasian | AA | Asian | Hispanic | | |
| Control | 82 | 50.0% | 50.0% | 50.0% | 45.1% | 4.9% | 0 | 35.3 | 27.5 |
| Transplant | 39 | 56.4% | 43.6% | 57.6% | 44.1% | 1.7% | 1.7% | 47.5 | 28.6 |

TABLE 5

Transplant group characteristics

| Transplant group: | All (n = 39) | Caucasian (n = 19) | African-American (n = 18) |
| --- | --- | --- | --- |
| Diagnoses | | | |
| Diabetes/Hypertension | 51.3% | 47.4% | 61.1% |
| PCKD | 18.0% | 26.3% | 11.1% |
| Glomerular disease | 18.0% | 15.8% | 11.1% |
| Other | 12.8% | 10.5% | 16.7% |
| Type of Transplant | | | |
| Living, related | 21.1% | 36.8% | 5.6% |
| Living, unrelated | 13.2% | 15.8% | 11.1% |
| Deceased | 65.8% | 47.4% | 83.3% |
| Time Since Transplant | | | |
| mean | 22 +/− 6 | 19 +/− 8 | 25 +/− 10 |
| range | 1-175 | 1-133 | 1-167 |
| <1yr | 61% | 74% | 67% |
| >1yr | 31% | 26% | 33% |

56% of the group was male, while 44% was female. The average age and BMI of the post-transplant patients was slightly higher than the control group at 47.5 years and 28.6, respectively. 2 patients were of Asian descent, 18 were Caucasian (caucasian), and 19 self-reported as African American (African-American), a racial distribution that was similar to the control group. All patients were on standard post-transplant immune suppression, which included calcineurin inhibitors (31 received tacrolimus, while 8 were treated with cyclosporine A).

Consistent with previous reports, African-American patients were more likely to have been diagnosed with hypertension and/or diabetes than caucasian patients, and were more likely to have received kidneys from deceased donors rather than living donors. However, other characteristics including kidney function were comparable between caucasian and African-American patients (MDRD estimated GFR was 56.9 for caucasian and 56.4 for African-American subjects), Basal and anti-CD3/CD28-stimulated calcineurin activity was measured in T cells isolated from transplant patients, as shown in FIG. 22C. Unlike the control group, CD3/CD28 antibodies failed to induce a significant increase in calcineurin activity (paired T-test). The mean percent increase in non-transplant control subjects' calcineurin activity was 41% compared to only 8% for transplant patients, a significant difference ($p<0.01$) (FIG. 22D).

Example 15

While calcineurin inhibitors have been instrumental in improving short-term graft survival, a variety of factors including race have been demonstrated to effect long-term outcomes. Calcineurin activity of caucasian and African-American transplant patients was therefore analyzed to determine if there were differences in basal activity or anti-CD3/CD28 co-stimulation. caucasian transplant patients had significantly higher basal levels of calcineurin activity compared to both controls and to African-American transplant patients (ANOVA, Tukey's post-test), as shown in FIG. 23A. In contrast, basal calcineurin activity in the African-American group was not different from that of controls. Stimulation of calcineurin activity was also determined for caucasian and African-American transplant patients. There was no significant increase in calcineurin activity in response to anti-CD3/CD28 co-stimulation in T cells from caucasian patients. In contrast, stimulation of calcineurin activity in African-American transplant patients was a mean of 36%, a level not significantly difference from control subjects (ANOVA, Tukey's post-test) (FIG. 23B). Trough blood levels of FK506 for both caucasian and African-American transplant patients were obtained at the time of T cell isolation. There was no significant difference between the mean trough FK506 blood level of 11.4+/−0.7 for caucasians and 12.0+/−0.9 for African-Americans or between cyclosporine A levels of 227+/−99.9 for caucasian and 131+/−31.4 for African-American patients.

To further investigate the relationship between calcineurin activity and race, control subjects were analyzed by self-reported racial group. Four volunteers were identified as Asian, 41 as Caucasian and 37 as African American, a distribution that was comparable to the transplant cohort. Anti-CD3/CD28 co-stimulation resulted in a significant increase in calcineurin activity in both caucasian and African-American controls. The percent increases were not different between the two groups, nor were the basal, unstimulated levels of calcineurin activity. Stimulation of calcineurin activity by anti-CD3/CD28 in caucasian controls was inhibited by both cyclosporine and FK506 (FIG. 23C). However, neither cyclosporine A nor FK506 significantly reduced calcineurin activity in African-American volunteers (FIG. 23D).

Example 16

Since factors that may modify long-term graft survival such as cytokine expression are also known to vary by race, it was possible that changes in calcineurin activity correlate with changes in cytokine expression. Cytokine production by isolated T cells from a subset of patients (N=6; 3 caucasian and 3 African-American) was examined using a Panomics cytokine array. Results of cytokine levels were compared by linear regression analyses with both basal and fold stimulation of calcineurin in the same patients. FIGS. 24A and 24B show that IL-4 and IL-10 were inversely correlated with changes in basal calcineurin. Higher levels of cytokine expression correlate with lower basal calcineurin activity. In contrast, FIGS. 24C and 24D show that IL-2 and TGFβ were positively correlated with changes in anti-CD3/CD28-stimulation of calcineurin. Higher cytokine expression is correlated with higher levels of calcineurin stimulation. IL-3 correlated with both changes in basal and changes in fold stimulation while other cytokines including IFNγ, TNFα, and IL-6 showed a small or no association with calcineurin and are described in Table 6.

TABLE 6

Correlation of basal and stimulated calcineurin with cytokine regulation

| T cell cytokine production | Calcineurin (basal) | | Calcineurin (fold increase) | |
|---|---|---|---|---|
| | $R^2$ | P value | $R^2$ | P value |
| TGFP | .018 | 1∞ | .637 | .057 |
| IFNγ | .419 | .165 | .138 | .468 |
| TNFa | .057 | .076 | .145 | .457 |
| IL-2 | .263 | .298 | .807 | .015* |
| IL-3 | .883 | .005* | .785 | .019* |
| IL-4 | .639 | .056 | .383 | .190 |
| IL-6 | .502 | .115 | .187 | .392 |
| IL-10 | .660 | .048* | .311 | .250 |

FIGS. 24A-24D, and Table 6 demonstrate that while increased T cell expression of some cytokines are associated with lower basal levels of calcineurin, other cytokines including TGFβ appear to be regulated concomitantly with stimulated calcineurin activity.

Example 17

FIGS. 25A-25D show that in the control and transplant cohorts recruited for this study, serum TGFβ levels were higher in transplant patients compared to control subjects (FIG. 25A). The mean levels of IFNγ were also lower in transplant patients, although the change did not reach significance (FIG. 25B). Similarly, African-American transplant patients had significantly higher levels of serum TGFβ compared to caucasian transplant patients (FIG. 25C), while there was no difference in the levels serum IFNγ (FIG. 25D).

TABLE 7

Multivariate Analysis by control/transplant group

| | CI dose | Race | Gender | Age | BMI |
|---|---|---|---|---|---|
| Control Group | | | | | |
| Basal activity | n/a | ns | ns | ns*[1] | ns |
| Stimulation | n/a | ns | $p < 0.05$ | ns | ns*[2] |
| Sensitivity to calcineurin | n/a | $p < 0.05$ | ns | ns | ns |
| Transplant Group | | | | | |
| Basal activity | ns | $p < 0.05$ | ns | ns | $p < 0.05$*[4] |
| Stimulation | ns | $p < 0.01$ | $p < 0.05$ | ns*[3] | ns |

*[1]trend for caucasian($p < .1$)
*[2]$p < 0.05$ for caucasian
*[3]$p < 0.01$ for caucasian
*[4]$p < 0.05$ for caucasian, ns for African-American

We claim:

1. A method for determining the response on calcineurin activity of a human or animal subject to an immunosuppressive therapeutic agent, the method comprising:
   (i) obtaining an isolated population of T cells from a human or animal subject in receipt of an immunosuppressive therapeutic agent;
   (ii) lysing the isolated population of T cells;
   (iii) dividing the lysed isolated T cell population into at least a first aliquot and a second aliquot;
   (iv) determining a first level of calcineurin activity in the first aliquot of lysed T cells;
   (v) contacting the second aliquot of lysed T cells with a composition comprising a T cell receptor agonist and then determining a second level of calcineurin activity in the second aliquot of lysed T cells; and
   (vi) comparing the first and the second levels of calcineurin activity as determined in steps (iv) and (v) respectively, whereby the ratio of the first and the second levels of calcineurin activity indicates the degree of responsiveness on calcineurin activity by the human or animal subject to the immunosuppressive therapeutic agent;
   wherein the first and the second levels of calcineurin activity are determined by a fluorimetric assay;
   wherein the fluorimetric assay comprises the steps of:
      (a) contacting in a reaction mix the first aliquot of lysed T cells and a fluorescently labeled phosphorylated target peptide substrate capable of being dephosphorylated by calcineurin, wherein the target peptide comprises an amino acid sequence of SEQ ID NO.: 2, under conditions allowing calcineurin to dephosphorylate the target peptide;
      (b) contacting the reaction mix with a titanium oxide matrix, thereby partitioning phosphorylated target peptide from dephosphorylated target peptide;
      (c) determining a fluorescence intensity of the fluorescently labeled dephosphorylated target peptide; and
      (d) correlating the fluorescence intensity to the calcineurin activity, said correlating step comprising:
         (i) providing a test sample, wherein the test sample comprises a known amount of calcineurin activity, and repeating steps (a)-(c) on said test sample, thereby obtaining a value of a test fluorescence intensity corresponding to the known amount of the calcineurin; and
         (ii) comparing the fluorescence intensity of the fluorescently labeled dephosphorylated target peptide generated from the first aliquot of lysed T cells with the value of the test fluorescence intensity obtained with the known amount of calcineurin, thereby determining an amount of calcineurin activity in the first aliquot of isolated T cells; and
      (e) repeating steps (a)-(d) for the second aliquot of lysed T cells
   wherein the target peptide is capable of being specifically dephosphorylated by the β-isoform of calcineurin and comprises SEQ ID NO.: 2, wherein the S-6 position is phosphorylated.

2. The method of claim 1, wherein the T cell agonist is an anti-CD3-specific antibody.

3. The method of claim 1, wherein the composition comprising a T cell receptor agonist further comprises a T cell co-stimulator.

4. The method of claim 3, wherein the T cell co-stimulator is an anti-CD28-specific antibody.

5. The method of claim 1, wherein the composition comprising a T cell receptor agonist does not comprise a T cell co-stimulator.

6. The method of claim 1, wherein the human or animal subject is a transplant recipient.

7. The method of claim 1, wherein the assay method is configured for high-throughput screening of a plurality of test samples.

8. The method of claim 1, wherein the assay method is configured for automated high-throughput screening of a plurality of test samples.

9. A method for determining the response on calcineurin activity of a human or animal subject to an immunosuppressive therapeutic agent, the method comprising:
   (i) obtaining an isolated population of T cells from a human or animal subject in receipt of an immunosuppressive therapeutic agent;
   (ii) lysing the isolated population of T cells;
   (iii) dividing the lysed isolated T cell population into at least a first aliquot and a second aliquot;
   (iv) determining a first level of calcineurin activity in the first aliquot of lysed T cells;
   (v) contacting the second aliquot of lysed T cells with a composition comprising a T cell receptor agonist and then determining a second level of calcineurin activity in the second aliquot of lysed T cells; and
   (vi) comparing the first and the second levels of calcineurin activity as determined in steps (iv) and (v) respectively, whereby the ratio of the first and the second levels of calcineurin activity indicates the degree of responsiveness on calcineurin activity by the human or animal subject to the immunosuppressive therapeutic agent;
   wherein the first and the second levels of calcineurin activity are determined by a Fluorescence Resonance Energy Transfer assay;
   wherein the Fluorescence Resonance Energy Transfer assay comprises:
     (a) providing an assay reaction mix comprising: a target peptide comprising an amino acid sequence specifically recognized by calcineurin, wherein the target peptide comprises an amino acid sequence of SEQ ID NO.: 2, a phosphate group conjugated to said target peptide, and a first fluorophore species conjugated to said target peptide; a buffer mix configured to allow calcineurin to dephosphorylate the target peptide; and the first aliquot of lysed T cells;
     (b) incubating the assay reaction mix under conditions suitable for calcineurin to dephosphorylate the target peptide;
     (c) contacting the incubated reaction mix with titanium oxide, said titanium oxide having a second fluorophore species conjugated thereon, under conditions suitable for the titanium oxide to bind to a phosphorylated target peptide but not to a dephosphorylated target peptide;
     (d) illuminating the titanium oxide at an excitation wavelength of the second fluorophore species, whereby the second fluorophore species emits a first fluorescence, said first fluorescence exciting the first fluorophore species by Fluorescence Resonance Energy Transfer, thereby inducing the emission of a second fluorescence from the first fluorophore species, said second fluorescence having a wavelength different from the wavelength of the first fluorescence;
     (e) selectively detecting the second fluorescence, thereby detecting binding of phosphorylated target peptide to titanium oxide;
     (f) determining a fluorescence intensity of the second fluorescence; and
     (g) correlating the fluorescence intensity of the second fluorescence to an amount of calcineurin activity, said correlating step comprising:
       (i) providing a test sample comprising a known amount of calcineurin activity, and repeating steps (a)-(f) on said test sample, thereby obtaining a value of a test fluorescence intensity corresponding to the known amount of the calcineurin;
       (ii) comparing the fluorescence intensity generated from the first aliquot of lysed T cells with the value of the test fluorescence intensity obtained with the known amount of calcineurin, thereby determining the amount of calcineurin activity in the first aliquot of isolated T cells; and
     (h) repeating steps (a)-(g) for the second aliquot of lysed T cells
   wherein the target peptide is capable of being specifically dephosphorylated by the β-isoform of calcineurin and comprises SEQ ID NO.: 2, wherein the S-6 position is phosphorylated.

10. The method of claim 9, wherein the titanium oxide is formulated as micro-beads, and wherein the micro-beads are suspended in the assay reaction mix.

11. The method of claim 9, wherein the assay method is configured for automated high-throughput screening of a plurality of test samples.

* * * * *

UNITED STATES PATENT AND TRADEMARK OFFICE
CERTIFICATE OF CORRECTION

PATENT NO. : 8,546,095 B2  
APPLICATION NO. : 12/690146  
DATED : October 1, 2013  
INVENTOR(S) : James Tumlin et al.

Page 1 of 1

It is certified that error appears in the above-identified patent and that said Letters Patent is hereby corrected as shown below:

In the Specification

Please replace Col 1, lines 25 to 28 as follows:

-- This invention was made with government support under Grant No. R01 DK066422 awarded by the National Institutes of Health. The government has certain rights in the invention. --

Signed and Sealed this  
Fourth Day of March, 2014

Michelle K. Lee  
*Deputy Director of the United States Patent and Trademark Office*

UNITED STATES PATENT AND TRADEMARK OFFICE
CERTIFICATE OF CORRECTION

Page 1 of 1

PATENT NO. : 8,546,095 B2
APPLICATION NO. : 12/690146
DATED : October 1, 2013
INVENTOR(S) : James Tumlin et al.

It is certified that error appears in the above-identified patent and that said Letters Patent is hereby corrected as shown below:

In the Specification

Please replace Col 1, lines 25 to 28 as follows:

-- This invention was made with government support under Grant Nos. R01 DK066422 and R01 DK038842 awarded by the National Institutes of Health. The government has certain rights in the invention. --

This certificate supersedes the Certificate of Correction issued March 4, 2014.

Signed and Sealed this
Fifteenth Day of April, 2014

Michelle K. Lee
*Deputy Director of the United States Patent and Trademark Office*

SEQUENCE LISTING

<160> NUMBER OF SEQ ID NOS: 2

<210> SEQ ID NO 1
<211> LENGTH: 19
<212> TYPE: PRT
<213> ORGANISM: Artificial
<220> FEATURE:
<223> OTHER INFORMATION: Calcineurin peptide substrate isoform

<400> SEQUENCE: 1

Asp Leu Asp Val Pro Ile Pro Gly Arg Phe Asp Arg Arg Val Ser Val
1               5                   10                  15

Ala Ala Glu

<210> SEQ ID NO 2
<211> LENGTH: 16
<212> TYPE: PRT
<213> ORGANISM: Artificial
<220> FEATURE:
<223> OTHER INFORMATION: Calcineurin peptide substrate beta isoform

<400> SEQUENCE: 2

Ala Ser Pro Gln Thr Ser Pro Trp Gln Ser Pro Ala Val Ser Pro Lys
1               5                   10                  15